United States Patent
Meng et al.

(10) Patent No.: US 7,589,088 B2
(45) Date of Patent: Sep. 15, 2009

(54) PYRIMIDINE-BASED INHIBITORS OF DIPEPTIDYL PEPTIDASE IV AND METHODS

(75) Inventors: Wei Meng, Pennington, NJ (US); Lawrence G. Hamann, Cherry Hill, NJ (US); Robert Brigance, Levittown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 589 days.

(21) Appl. No.: 11/314,795

(22) Filed: Dec. 21, 2005

(65) Prior Publication Data

US 2006/0142576 A1   Jun. 29, 2006

Related U.S. Application Data

(60) Provisional application No. 60/640,110, filed on Dec. 29, 2004.

(51) Int. Cl.
  *C07D 239/26* (2006.01)
  *A61K 31/505* (2006.01)

(52) U.S. Cl. ............... 514/227.8; 514/256; 544/60; 544/242

(58) Field of Classification Search ............ 544/60, 544/242; 514/227.8, 256
See application file for complete search history.

(56) References Cited

U.S. PATENT DOCUMENTS

| 3,674,836 | A | 7/1972 | Creger |
| 3,983,140 | A | 9/1976 | Endo et al. |
| 4,027,009 | A | 5/1977 | Grier et al. |
| 4,231,938 | A | 11/1980 | Monaghan et al. |
| 4,346,227 | A | 8/1982 | Terahara et al. |
| 4,448,784 | A | 5/1984 | Glamkowski et al. |
| 4,450,171 | A | 5/1984 | Hoffman et al. |
| 4,499,289 | A | 2/1985 | Baran et al. |
| 4,613,610 | A | 9/1986 | Wareing |
| 4,647,576 | A | 3/1987 | Hoefle et al. |
| 4,681,893 | A | 7/1987 | Roth |
| 4,686,237 | A | 8/1987 | Anderson |
| 4,759,923 | A | 7/1988 | Buntin et al. |
| 4,871,721 | A | 10/1989 | Biller |
| 4,924,024 | A | 5/1990 | Biller |
| 5,006,530 | A | 4/1991 | Angerbauer et al. |
| 5,011,930 | A | 4/1991 | Fujikawa et al. |
| 5,177,080 | A | 1/1993 | Angerbauer et al. |
| 5,260,440 | A | 11/1993 | Hirai et al. |
| 5,273,995 | A | 12/1993 | Roth |
| 5,346,701 | A | 9/1994 | Heiber et al. |
| 5,354,772 | A | 10/1994 | Kathawala |
| 5,385,929 | A | 1/1995 | Bjorge et al. |
| 5,488,064 | A | 1/1996 | Sher |
| 5,491,134 | A | 2/1996 | Sher et al. |
| 5,506,219 | A | 4/1996 | Robl |
| 5,541,204 | A | 7/1996 | Sher et al. |
| 5,594,016 | A | 1/1997 | Ueno et al. |
| 5,595,872 | A | 1/1997 | Wetterau, II et al. |
| 5,612,359 | A | 3/1997 | Murugesan |
| 5,614,492 | A | 3/1997 | Habener |
| 5,631,224 | A | 5/1997 | Efendic et al. |
| 5,686,104 | A | 11/1997 | Mills et al. |
| 5,691,322 | A | 11/1997 | Robl |
| 5,712,279 | A | 1/1998 | Biller et al. |
| 5,712,396 | A | 1/1998 | Magnin et al. |
| 5,739,135 | A | 4/1998 | Biller et al. |
| 5,753,675 | A | 5/1998 | Wattanasin |
| 5,760,246 | A | 6/1998 | Biller et al. |
| 5,770,615 | A | 6/1998 | Cheng et al. |
| 5,776,983 | A | 7/1998 | Washburn et al. |
| 5,827,875 | A | 10/1998 | Dickson, Jr. et al. |
| 5,885,983 | A | 3/1999 | Biller et al. |
| 5,962,440 | A | 10/1999 | Sulsky |
| 6,043,265 | A | 3/2000 | Murugesan et al. |
| 6,395,767 | B2 | 5/2002 | Robl et al. |
| 6,548,529 | B1 | 4/2003 | Robl et al. |
| 6,653,314 | B2 | 11/2003 | Cheng et al. |
| 6,995,183 | B2 | 2/2006 | Hamann et al. |

FOREIGN PATENT DOCUMENTS

| EP | 0 142 146 | 11/1984 |
| EP | 0 221 025 | 10/1986 |
| FR | 2 596 393 | 5/1986 |
| GB | 2 205 837 | 5/1988 |
| WO | WO86/03488 | 6/1986 |
| WO | WO86/07054 | 12/1986 |
| WO | WO96/38144 | 12/1996 |

(Continued)

OTHER PUBLICATIONS

Wiedeman et al., Dipeptidyl peptidase IV inhibitors for the treatment of impaired glucose tolerance and type 2 diabetes, Current Opinion in Investigational Drugs, vol. 4, No. 4, pp. 412-420 (2003).*

(Continued)

*Primary Examiner*—Deepak Rao
(74) *Attorney, Agent, or Firm*—Maureen S. Gibbons; Burton Rodney

(57) ABSTRACT

Compounds are provided having the formula (I)

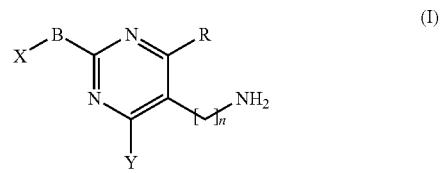

wherein R, B, X and Y are as defined herein.

15 Claims, No Drawings

FOREIGN PATENT DOCUMENTS

| | | |
|---|---|---|
| WO | WO97/12613 | 4/1997 |
| WO | WO97/12615 | 4/1997 |
| WO | WO97/21993 | 6/1997 |
| WO | WO99/00353 | 1/1999 |
| WO | WO99/38501 | 8/1999 |
| WO | WO99/46272 | 9/1999 |
| WO | WO99/61431 | 12/1999 |
| WO | WO99/67278 | 12/1999 |
| WO | WO99/67279 | 12/1999 |
| WO | WO00/01389 | 1/2000 |
| WO | WO01/21602 | 3/2001 |
| WO | WO01/68603 | 9/2001 |
| WO | WO03/033671 | 4/2003 |
| WO | WO03/068757 | 8/2003 |
| WO | WO 2004/087679 | * 10/2004 |

OTHER PUBLICATIONS

Villhauer et al., DPP-IV inhibition and Therapeutic Potential, Annual Reports in Chemistry, 36, pp. 191-200 (2001).*

Peters, Jens-Uwe, et al., "An aminomethylpyrimidine DPP-IV inhibitor with improved properties", Bioorganic & Medicinal Chemistry Letters, vol. 14, pp. 3575-3578 (2004).

Peters, Jens-Uwe, et al., "Aminomethylpyrimidines as novel DPP-IV inhibitors: A $10^5$-fold activity increase by optimization of aromatic substituents", Bioorganic & Medicinal Chemistry Letters, vol. 14, pp. 1491-1493 (2004).

Ashworth, D. et al., "2-Cyanopyrrolidides as Potent, Stable Inhibitors of Dipeptidyl Peptidase IV", Bioorganic & Medicinal Chemistry Letters, vol. 6(10), pp. 1163-1166 (1996).

Ashworth, D. et al., "4-Cyanothiazolidides as Very Potent, Stable Inhibitors of Dipeptidyl Peptidase IV", Bioorganic & Medicinal Letters, vol. 6(22), pp. 2745-2748 (1996).

Biller, S. et al., "Isoprenoid (Phosphinylmethyl) phosphonates as Inhibitors of Squalene Synthetase", J. of Medicinal Chemistry, vol. 31(10), pp. 1869-1871 (1988).

Biller, S. et al. "Squalene Synthase Inhibitors", Current Pharmaceutical Design, vol. 2, pp. 1-40 (1996).

Corey, E. et al., "Application of Unreactive Analogs of Terpenoid Pyrophosphates to Studies of Multistep Biosynthesis. Demonstration that "Presqualene Pyrophosphate" Is an Essential Intermediate on the Path to Squalene", J. American Chemical Society, vol. 98(5), pp. 1291-1293 (1976).

Cornicelli, J. et al., "15-Lipoxygenase and Its Inhibition: A Novel Therapeutic Target for Vascular Disease", Current Pharmaceutical Design, vol. 5, pp. 11-20 (1999).

Hara, S., "Ileal $Na^+$/bile acid cotransporter inhibitors", Drugs of the Future, vol. 24(4), pp. 425-430 (1999).

Hart, D. et al., "Preparation of Primary Amines and 2-Azetidinones via N-Trimethylsilyl Imines", J. Org. Chem., vol. 48(3), pp. 289-294 (1983).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16(1), pp. 16-30 (1998).

Hughes, T. et al., "NVP-DPP728 (1-[[[2-[(5-Cyanopyridin-2-yl)amino]ethyl]amino]acetyl]-2-cyano-(S)-pyrrolidine), a Slow-Binding Inhibitor of Dipeptidyl Peptidase IV", Biochemistry, vol. 38, pp. 11597-11603 (1999).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure*", J. Clinical Endocrinology and Metabolism, vol. 82(3), pp. 727-734 (1997).

Krause, B. et al., "ACAT Inhibitors: Physiologic Mechanisms for Hypolipidemic and Anti-Atherosclerotic Activities in Experimental Animals", Inflammation: Mediators and Pathways, pp. 173-198 (1995).

McClard, R. et al., "Novel Phosphonylphosphinyl (P-C-P-C) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-60 (PPAR-$\alpha$) and PPAR-$\gamma$", Diabetes, vol. 47, pp. 1841-1847 (1998).

Nicolosi, R. et al., "The ACAT inhibitor, CI-1011 is effective in the prevention and regression of aortic fatty streak area in hamsters", Atherosclerosis, vol. 137, pp. 77-85 (1998).

Ortiz de Montellano, P. et al., "Inhibition of Squalene Synthetase by Farnesyl Pyrophosphate Analogues", J. of Medicinal Chemistry, vol. 20(2), pp. 243-249 (1977).

Rosenblum, S. et al., "Discovery of 1-(4-Flurophenyl)-(3R)-[3-(4-flurophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980(1998).

Salisbury, B. et al., "Hypocholesterolemic activity of a novel inhibitor of cholesterol absorption, SCH 48461", Atherosclerosis, vol. 115, pp. 45-63 (1995).

Sendobry, S, et al., "Attenuation of diet-induced atherosclerosis in rabbits with a highly selective 15-lipoxygenase inhibitor lacking significant antioxidant properties", British J. of Pharmacology, vol. 120, pp. 1199-1206 (1997).

Sliskovic, D. et al., "ACAT Inhibitors: Potential Anti-atherosclerotic Agents", Current Medicinal Chemistry, vol. 1, pp. 204-225 (1994).

Smith, C. et al., "RP73163: A Bioavailable Alkylsulphinyl-Diphenylimidazole ACT Inhibitor", Bioorganic & Medicinal Chemistry Letters, vol. 6(1), pp. 47-50 (1996).

Sorbera, L. et al., "Treatment of Lipoprotein Disorders ACAT Inhibitor", Drugs of the Future, vol. 24(1), pp. 9-15 (1999).

Stout, D., "Inhibitors of Acyl-CoA: Cholesterol O-Acyl Transferase (ACAT) as Hypocholesterolemic Agents.6. The First Water-Soluble ACAT Inhibitor with Lipid-Regulating Activity. Inhibitors of Acyl-CoA: Cholesterol Acyltransferase (ACAT). 7. Development of a Series of Substituted N-Phenyl-N-[(1- phenylcyclopentyl)-methyl]ureas with Enchanced Hypocholestrolemic Activity", Chemtracts-Organic Chemistry, vol. 8, pp. 359-362 (1995).

Yamada, M. et al., "A Potent Dipeptide Inhibitor of Dipeptidyl Peptidase IV", Bioorganic & Medicinal Chemistry Letters, vol. 8, pp. 1537-1540 (1998).

Morrison, J. et al., "The Behavior and Significance of Slow-Binding Enzyme Inhibitors", Advances in Enzymology, vol. 61, pp. 201-301- (1988).

* cited by examiner

SEQUENCE LISTING

```
<160> NUMBER OF SEQ ID NOS: 4

<210> SEQ ID NO 1
<211> LENGTH: 18
<212> TYPE: DNA
<213> ORGANISM: Homo sapiens

<400> SEQUENCE: 1
acgccgacga tgaagaca                                                 18

<210> SEQ ID NO 2
<211> LENGTH: 20
<212> TYPE: DNA
<213> ORGANISM: Homo sapiens

<400> SEQUENCE: 2
aggtaaagag aaacattgtt                                               20
```

```
<210> SEQ ID NO 3
<211> LENGTH: 19
<212> TYPE: DNA
<213> ORGANISM: Homo sapiens

<400> SEQUENCE: 3
ggtaccagcg cagaggctt                                              19

<210> SEQ ID NO 4
<211> LENGTH: 27
<212> TYPE: DNA
<213> ORGANISM: Homo sapiens

<400> SEQUENCE: 4
ctcgagctaa ggtaaagaga aacattg                                     27
```

PYRIMIDINE-BASED INHIBITORS OF DIPEPTIDYL PEPTIDASE IV AND METHODS

CROSS-REFERENCE TO RELATED APPLICATIONS

This application claims the priority benefit of U.S. Provisional Application No. 60/640,110, filed Dec. 29, 2004, the disclosure of which is incorporated herein by reference in its entirety.

FIELD OF THE INVENTION

The present invention relates to pyrimidine-based inhibitors of dipeptidyl peptidase IV (DPP-4), and to a method for treating multiple diseases or disorders by employing such pyrimidine-based inhibitors alone, or in combination with another type of therapeutic agent.

BACKGROUND OF THE INVENTION

Dipeptidyl peptidase IV (DPP-4) is a membrane bound non-classical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7-36), glucagon) in vivo and has demonstrated proteolytic activity against a variety of other peptides (GHRH, NPY, QLP-2, VIP) in vitro.

GLP-1(7-36) is a 29 amino-acid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of type II diabetes and potentially obesity. To support this claim, exogenous administration of GLP-1(7-36) (continuous infusion) in diabetic patients has demonstrated efficacy in this patient population. Unfortunately GLP-1(7-36) is degraded rapidly in vivo and has been shown to have a short half-life in vivo (t½≈5 min). Based on a study of genetically bred DPP-4 KO mice and on in vivo/in vitro studies with selective DPP-4 inhibitors, DPP-4 has been shown to be the primary degrading enzyme of GLP-1(7-36) in vivo. GLP-1(7-36) is degraded by DPP-4 efficiently to GLP-1(9-36), which has been speculated to act as a physiological antagonist to GLP-1(7-36). Thus, inhibition of DPP-4 in vivo should potentiate endogenous levels of GLP-1(7-36) and attenuate formation of its antagonist GLP-1(9-36) and thus serve to ameliorate the diabetic condition.

DESCRIPTION OF THE INVENTION

In accordance with the present invention, compounds of formula (I) are provided

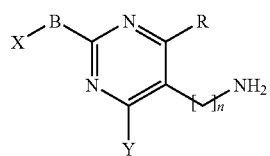

(I)

wherein:
n=1 or 2;
R is a substitutent selected from the group consisting of hydrogen (H), halogen, cyano (CN), $CF_3$, alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl and cycloheteroalkylalkyl, wherein any such substituent may optionally be substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

B is selected from the group consisting of a bond, oxygen (O), nitrogen (N) and $S(O)_m$;
m is 0, 1 or 2;
X is a substitutent selected from the group consisting of hydrogen (H), alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl and cycloheteroalkylalkyl, wherein any such substituent may optionally be substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

B—X taken together can be a halogen; and
Y is aryl, optionally substituted with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl.

The definition of formula I above includes all pharmaceutically acceptable salts, stereoisomers, and prodrug esters of formula I.

The compounds of formula I possess activity as inhibitors of DPP-4 in vivo and are useful in the treatment of diabetes and the micro- and macrovascular complications of diabetes such as retinopathy, neuropathy, nephropathy, and wound healing. Such diseases and maladies are also sometimes referred to as "diabetic complications".

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further provided is a method for treating or delaying the progression or onset of diabetes, especially type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of formula I is administered to a mammalian, e.g., human, patient in need of treatment.

The compounds of the invention can be used alone, in combination with other compounds of the present invention, or in combination with one or more other agent(s) active in the therapeutic areas described herein.

In addition, a method is provided for treating diabetes and related diseases as defined above and hereinafter, wherein a therapeutically effective amount of a combination of a compound of formula I and at least one other type of therapeutic agent, such as an antidiabetic agent and/or a hypolipidemic agent, is administered to a human patient in need of treatment.

Further embodiments of the invention include compounds of formula I wherein n is 1, or compounds of formula I having the structure:

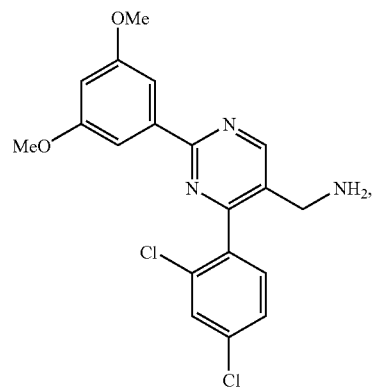

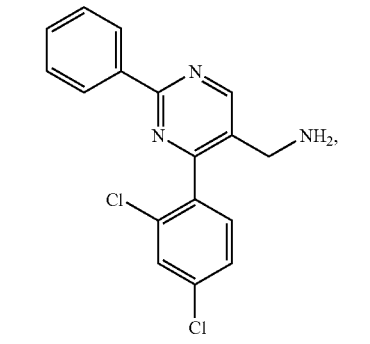

-continued

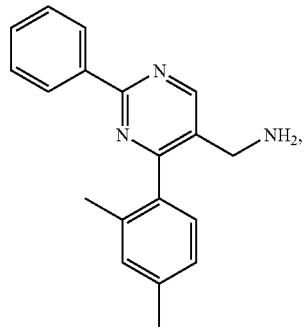

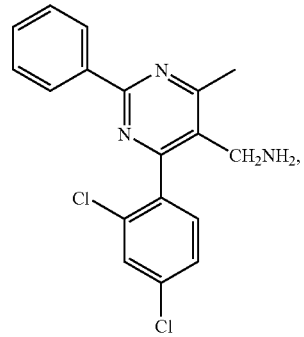

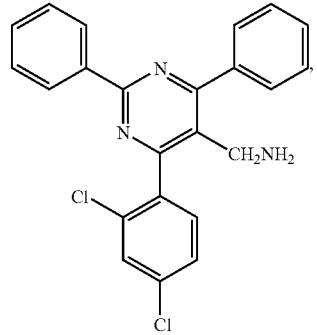

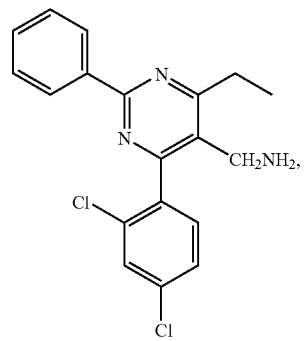

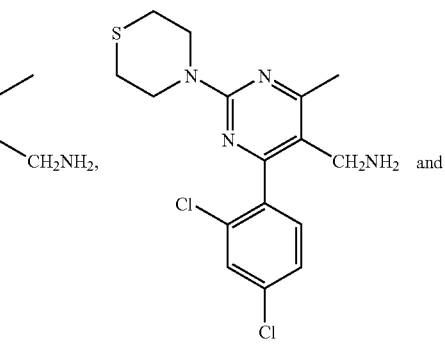

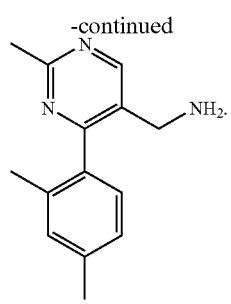

In the above method of the invention, the compound of formula (I) will be employed in a weight ratio to the antidiabetic agent or other type therapeutic agent (depending upon its mode of operation) within the range from about 0.01:1 to about 500:1, preferably from about 0.1:1 to about 100:1, more preferably from about 0.2:1 to about 10:1.

DETAILED DESCRIPTION OF THE INVENTION

Compounds of formula (I) may be generated by the methods as shown in the following reaction schemes and the descriptions thereof.

ylene chloride or THF at 0 to 60° C. for 2-48 hours. Ketonitriles of formula (4) can be prepared by combining the lithium anion of acetonitrile with an acid chloride of formula (2). Acetonitrile (3) can be deprotonated by a strong base such as n-BuLi in an anhydrous solvent such as THF or diethyl ether at low temperature to give the lithium anion of acetonitrile. Acrylnitriles of formula (5) can be prepared by methods known to those skilled in the art such as heating ketonitrile of formula (4) with dimethylformamide dimethylacetal in an inert solvent such as toluene at elevated temperature for 2-48 hours. Amidines of formula (6) can either be obtained through commercial sources or conveniently prepared by known methods. One example to make the amidines of formula (6) is to start with the corresponding nitrile, treating with HCl followed by $NH_3$ to provide amidines (6). Pyrimidines of formula (7) can be prepared by combining acrylonitriles (5) and amidines (6) by methods known in the art. For example, the process can be performed by heating an acrylonitrile (5) and an amidine (6) with a base such as NaOMe in methanol at room temperature to reflux for 2-48 hours. Aminomethylpyrimidines of formula (8) can be prepared from nitriles (7) through a reductive process. The reducing agents which may be used for this process include, but are not limited to LAH, $CoCl_{2/NaBH4}$, Raney Ni/$H_2$, and Pd/$H_2$.

Scheme 2 describes an alternative route to prepare aminomethylpyrimidines of formula (8).

SCHEME 1

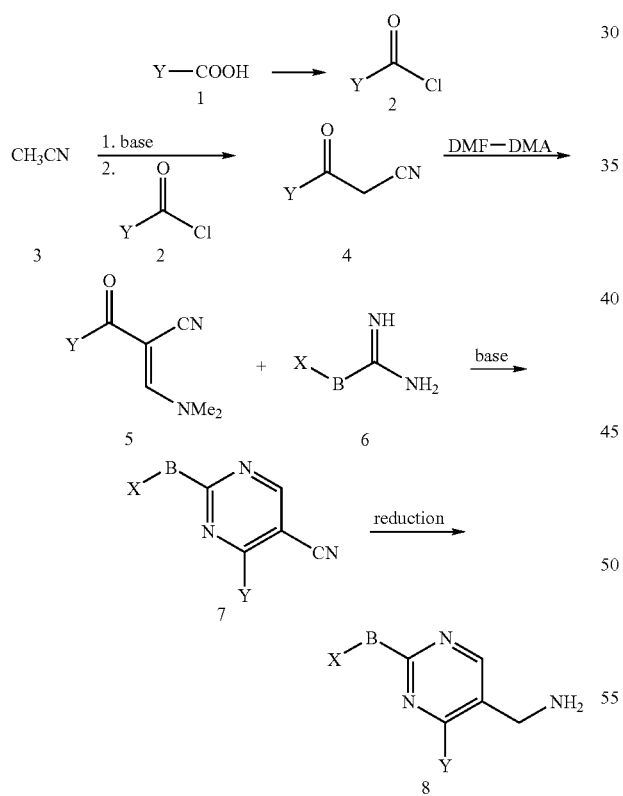

Scheme 1 provides a general route to prepare aminomethylpyrimidines of formula (8). Acid chlorides of formula (2) may be obtained from commercial sources, or alternatively generated by methods as described herein from the corresponding carboxylic acids of formula (1). For example, an acid chloride (2) can be formed by treating a carboxylic acid (1) with $(COCl)_2$ or $SOCl_2$ in an inert solvent such as meth-

SCHEME 2

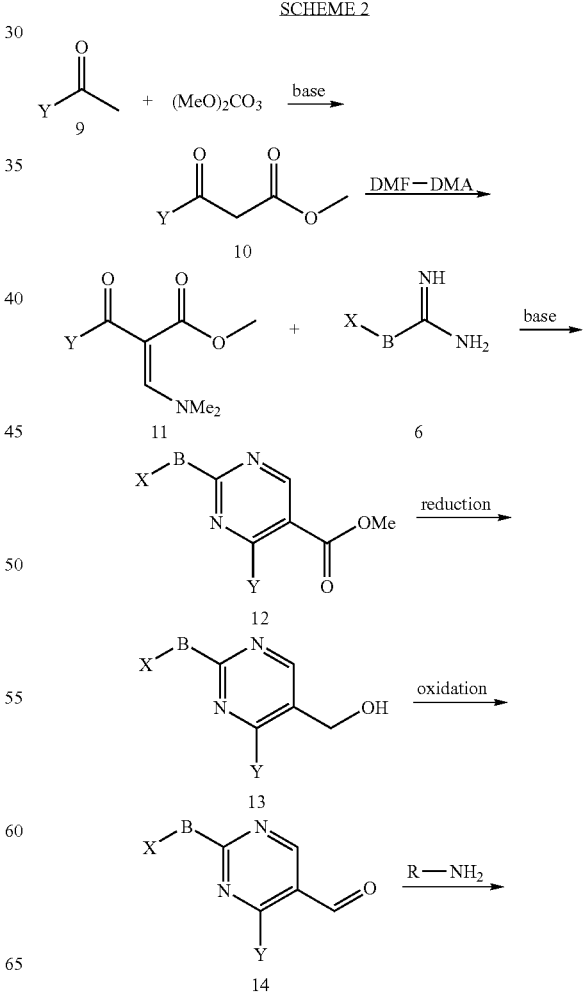

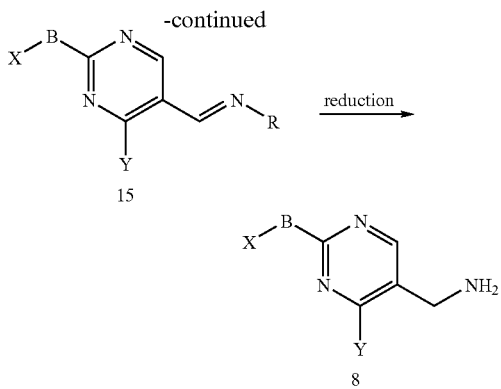

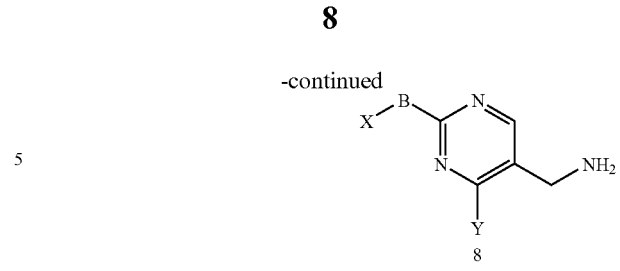

Ketoesters of formula (10) are known in the literature or can be conveniently prepared by known methods known. One example to prepare ketoesters of formula (10) is to combine a ketone (9) with a methylcarbonate and a base such as NaH in an inert solvent such as THF at ambient temperature for 2-24 hours. Acryloesters of formula (11) can be prepared by the same methods as described in Scheme 1 for acrylonitriles (5). Pyrimidine esters of formula (12) can be prepared by combining an acryloester (11) and an amidine (6) using the same methods as described in Scheme 1 for pyrimidines (7). Aminomethyl pyrimidines of formula (8) can then be prepared by those skilled in the art through a reduction/oxidation sequence on pyrimidine esters of formula (12) as described in scheme 2. The reducing agents that may be used to convert an ester of formula (12) to an alcohol of formula (13) include, but are not limited to DIBAL, LAH, and Red-Al. The oxidizing agents that may be used to convert an alcohol of formula (13) to an aldehyde of formula (14) include, but are not limited to Dess-Martin periodinane, Swern, PCC, $MnO_2$, and TPAP/NMO. As understood by those skilled in the art, formula (15) can be either an oxime or an imine, which can be conveniently prepared by combining an aldehyde of formula (14) with an amine or hydroxylamine. The reduction of compounds of formula (15) to aminomethylpyrimidines of formula (8) can be performed by using reducing agents such as Zn/HOAc, Pd/$H_2$, or Raney Ni/$H_2$.

Scheme 3 provides an alternative route of converting an alcohol of formula (13) to aminomethylpyrimidine of formula (8).

SCHEME 3

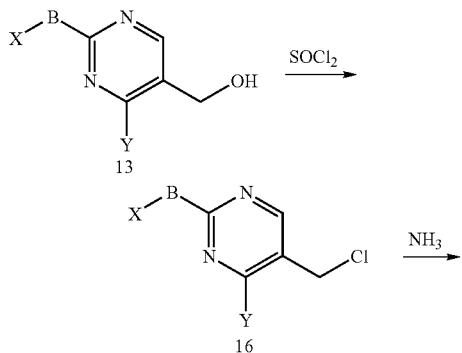

The chloropyrimidine of formula (16) can be formed from an alcohol of formula (13) by methods known to one skilled in the art. One example of such a transformation is to treat an alcohol (13) with $SOCl_2$ in an inert solvent such as $CH_2Cl_2$ at elevated temperature for 2-24 hours. The chloropyrimidines of formula (16) can be converted to aminomethylpyrimidines of formula (8) by bubbling $NH_3$ gas to a solution of chloropyrimidines (16) in a suitable solvent such as methanol.

Scheme 4 provides an alternative route for converting alcohols of formula (13) to aminomethylpyrimidines of formula (8).

SCHEME 4

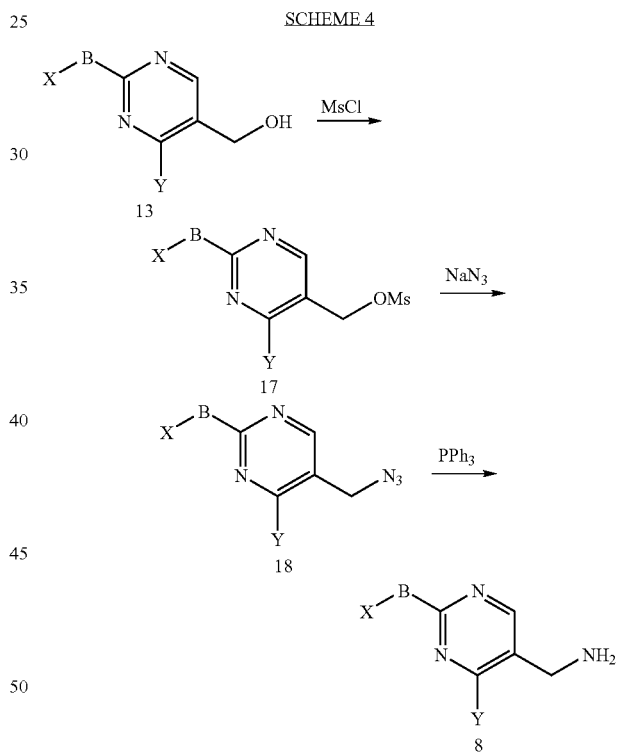

An alcohol of formula (13) can be converted to a suitable leaving group, such as a mesylate, by treating the alcohol (13) with methanesulfonyl chloride and a base such as triethylamine or pyridine in an inert solvent such as tetrahydrofuran or methylene chloride at 0 to 60° C. for 1 to 24 hours. The mesylates of formula (17) can then be converted to azides of formula (18) by known methods. One such set of conditions involves treatment of a mesylate (17) with sodium azide in an inert solvent such as DMF at room temperature to 100° C. for 1 to 24 hours. The azides of formula (18) can then be reduced to form aminomethylpyrimidines of formula (8). The reducing agents that may be used for this transformation include, but are not limited to triphenylphosphine, trialkylphosphine (including polymer supported phosphines), lithium aluminum hydride, hydrogen with palladium, and platinum containing catalysts.

Alkylated aminomethylpyrimidines of formula (19) can be prepared from aldehydes of formula (14) as described in scheme 5. One example of such a transformation can be found in: Hart, David J.; Kanai, Kenichi; Thomas, Dudley G.; Yang, Teng Kuei. Journal of Organic Chemistry (1983), 48(3), 289-94. Another example of such a transformation is to add a Grignard reagent (R—MgBr) to the aldehyde, followed by oxidation, imine/oxime formation and reduction as described in Scheme 3.

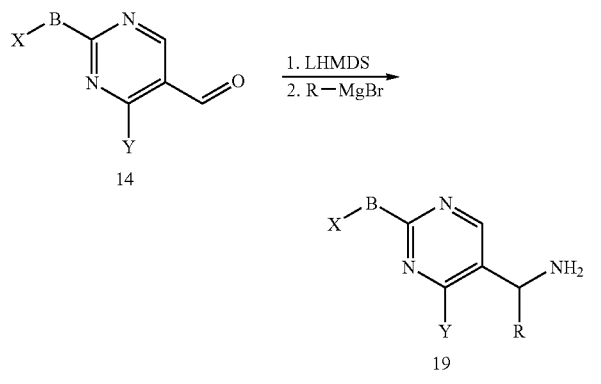

Scheme 6 describes a route to prepare 6-substituted aminomethylpyrimidines of formula (24).

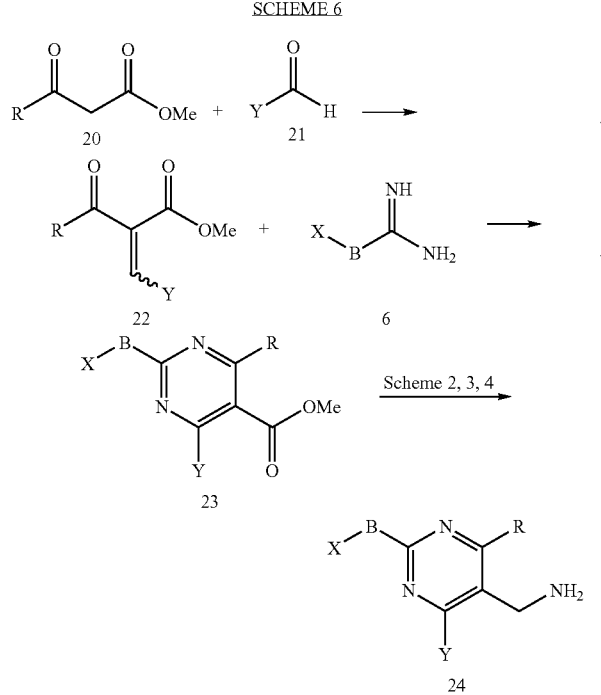

Keto esters of formula (20) can either be obtained from commercial sources or conveniently prepared by the methods described in Scheme 2. Acryloesters of formula (22) can be prepared by known methods by combining a ketoester of formula (20) and an aldehyde of formula (21). One example to prepare an acryloester of formula (22) is through a Knovenagel reaction. Pyrimidine esters of formula (23) can be prepared by methods known to those skilled in the art by combining acryloesters of formula (22) and amidines of formula (6) by known methods. For example, combining an acryloester of formula (22) and an amidine of formula (6) in the presence of a suitable base such as triethylamine, pyridine, NaOMe or KOAc in an inert solvent such as toluene, chloroform, benzene or DMF at elevated temperature gives pyrimidine esters of formula (23). The conversion of pyrimidine esters of formula (23) to aminomethylpyrimidines of formula (24) follows the same procedures as described in Schemes 2, 3 and 4.

Scheme 7 describes an alternative route to prepare aminomethylpyrimidines of formula (8).

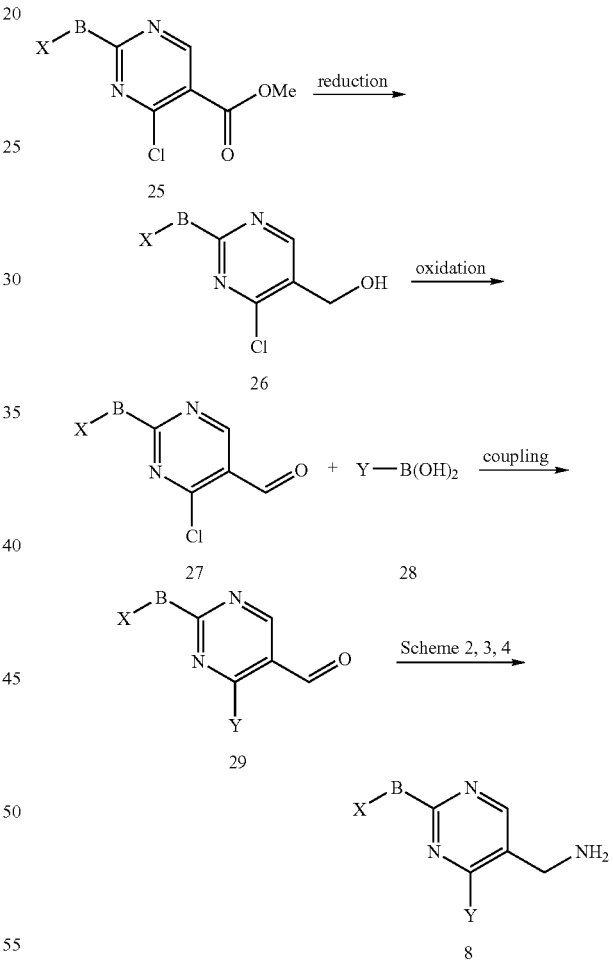

Pyrimidine esters of formula (25) can either be obtained through commercial sources or conveniently prepared by methods known in the art. The ester functionality of (25) can be converted to an alcohol of formula (26) by a reductive process. The reducing agents which may be used for this process include, but are not limited to LAH, DIBAL, Red-Al, and $NaBH_4$. The reaction can be performed by combining an ester (25) and the reducing agent in an inert solvent such as THF or toluene at −78° C. to elevated temperature for 2-24 hours. Pyrimidine aldehydes of formula (27) can be prepared from pyrimidine alcohols of formula (26) by an oxidative process. The oxidizing agents which may be used for this process include, but are not limited to PCC, Dess-Martin periodinane, Swern, and TPAP/NMO. The reaction can be performed in a solvent such as CH$_2$Cl$_2$, THF at −30° C. to ambient temperature for 2-24 hours. Pyrimidines of formula (29) can be prepared by combining a chloropyrimidine of formula (27) and a boronic acid of formula (28) by a Suzuki coupling process. Boronic acids of formula (28) can be obtained from commercial sources or conveniently prepared by methods known in the art. Examples of suitable palladium-catalyzed Suzuki coupling process can be found in: Palladium reagents and catalysts: innovations in organic synthesis, by Tsuji, Jiro; Palladium reagents in organic syntheses by Richard F. Heck. The aminomethylpyrimidines of formula (8) can be synthesized from compounds of formula (29) according the chemistry described in Schemes 2, 3 and 4.

2-Amino-substituted pyrimidines of formula (x) can be prepared by methods described in Scheme 8.

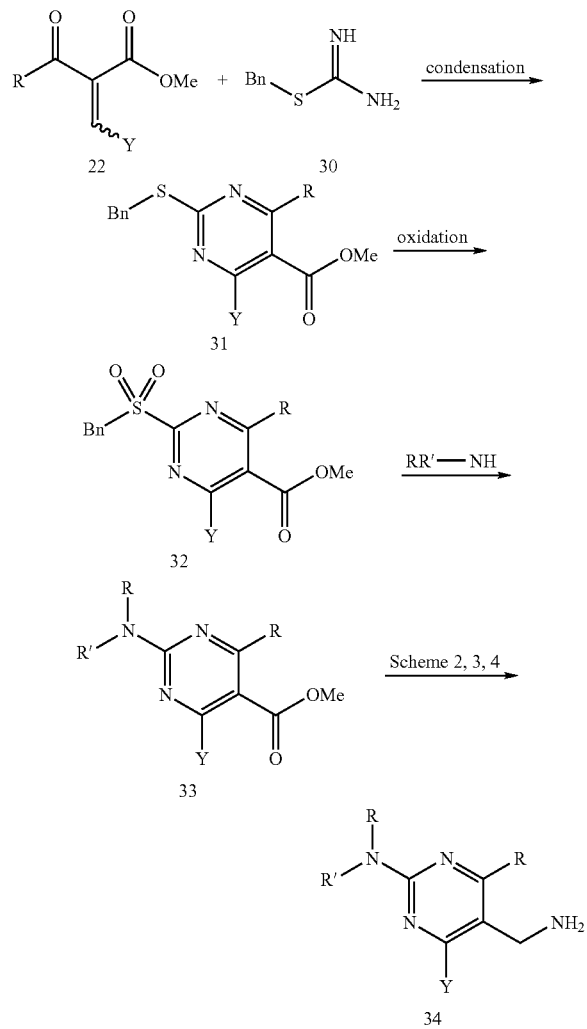

A ketoester of formula (22) can be condensed with an alkyl- or arylthioamidine such as (30) to give 2-alkylthiopyrimidines of formula (31) by known methods. One such set of conditions is to combine a ketoester of formula (22) with an amidine of formula (30) in a suitable solvent such as DMF at 20 to 100° C. for 1-72 hours. Molecular sieves can be added to facilitate the reaction. The alkylthio compound of formula (31) can be oxidized to an alkylsulfone of formula (32) by known methods. The oxidizing agents that may be used for this transformation include, but are not limited to mCPBA, hydrogen peroxide, PCC, and MnO$_2$. The alkylsulfone of formula (32) can then be displaced by amines to form a 2-aminosubstituted pyrimidine of formula (33). An example of one such set of conditions which may be used for this conversion is to combine a sulfone of formula (32) with a primary or secondary amine in a suitable solvent such as methylene chloride, THF or DMF at rt to 100° C. for 1 to 72 hours. The ester of formula (33) can be converted to an aminomethylpyrimidine of formula (34) by the same procedures as described in Schemes 2, 3, and 4.

DEFINITIONS

The following definitions apply to the terms as used throughout this specification, unless otherwise limited in specific instances.

Unless otherwise indicated, the term "alkyl" or "alk" as used herein alone or as part of another group includes both branched and straight-chain saturated aliphatic hydrocarbon radicals/groups having the specified number of carbon atoms. In particular, "Alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated. Unless otherwise constrained by the definition for the alkyl substituent, such alkyl groups can optionally be substituted with one or more substituents selected from a member of the group consisting of such as halo, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl", "carbocycle" or "carbocyclic" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes, for example cyclopropyl, cyclobutyl, cyclopentyl, cyclohexyl, cycloheptyl, cyclooctyl, cyclodecyl and cyclododecyl, cyclohexenyl,

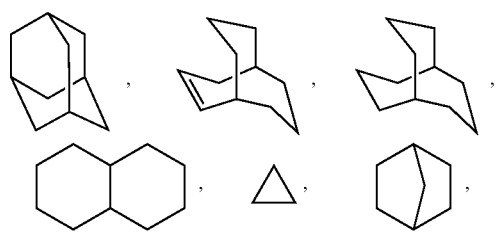

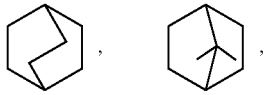

-continued any of which groups may be optionally substituted with 1 or more substituents such as of the substituents for described herein for alkyl or aryl.

The term "Aryl" or "Ar" as used herein alone or as part of another group refers to an unsaturated aromatic carbocyclic group of from 5 to 20 carbon atoms having a single ring (e.g., phenyl) or multiple condensed (fused) rings (e.g., naphthyl or anthryl). Representative examples include, but are not limited to, aromatic radicals such as phenyl, naphthyl, tetrahydronaphthyl, indane and biphenyl. Unless otherwise constrained by the definition for the aryl substituent, such aryl groups can optionally be substituted with one or more substituents selected from a member of the group consisting of hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, any of the alkyl substituents described herein, or substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "cycloheteroalkyl", "heterocyclo", "heterocyclic group" or "heterocyclyl" as used herein alone or as part of another group refers to a saturated or unsaturated group having a single ring, multiple condensed rings or multiple covalently joined rings, from 1 to 40 carbon atoms and from 1 to 10 hetero ring atoms, preferably I to 4 hetero ring atoms, selected from nitrogen, sulfur, phosphorus, and/or oxygen. Preferably, "Heterocycle" or "Heterocyclic group" means a stable 5 to 7 membered monocyclic or bicyclic or 7 to 10 membered bicyclic heterocyclic ring that may be saturated, partially unsaturated, or aromatic, and that comprises carbon atoms and from 1 to 4 heteroatoms independently selected from a member of the group consisting of nitrogen, oxygen and sulfur and wherein the nitrogen and sulfur heteroatoms are optionally be oxidized and the nitrogen heteroatom may optionally be quaternized, and including any bicyclic group in which any of the above-defined heterocyclic rings is fused to a benzene ring. The heterocyclic groups may be substituted on carbon or on a nitrogen, sulfur, phosphorus, and/or oxygen heteroatom, such as, but not limited to, the substituents described for alkyl or aryl herein, so long as the resulting compound is stable. For example:

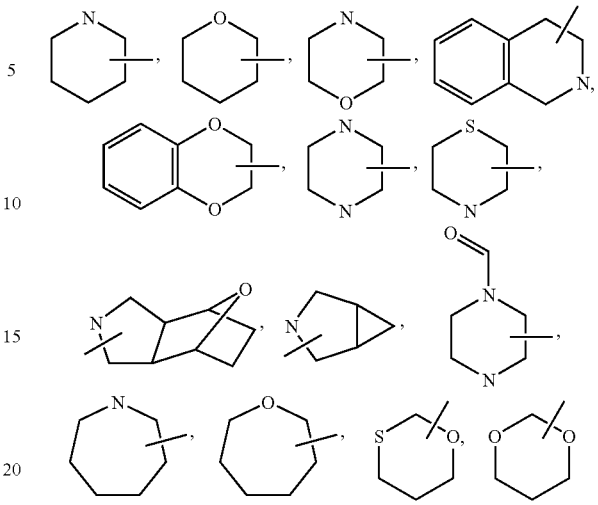

and the like.

"Heteroaryl" as used herein alone or as part of another group embraces unsaturated heterocyclic radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. Further, examples of heteroaryl groups include the following:

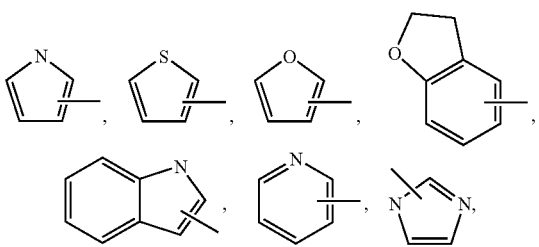

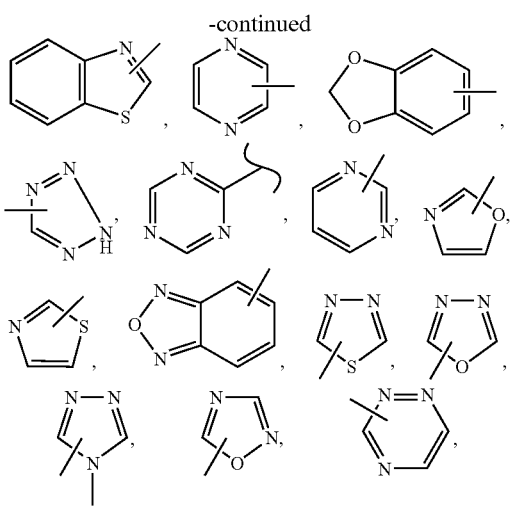

and the like. Unless otherwise constrained by the definition for the heteroaryl substituent, such heteroaryl groups can optionally be substituted with one or more substituents, such as those described for alkyl or aryl herein.

Unless otherwise indicated, the term "alkenyl" as used herein alone or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Optionally, said alkenyl group may be substituted with one or substituents, such as those substituents disclosed for alkyl.

Unless otherwise indicated, the term "alkynyl" as used herein alone or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like. Optionally, said alkynyl group may be substituted with one or substituents, such as those substituents disclosed for alkyl.

The term "cycloalkenyl" as employed herein alone or as part of another group refers to partially unsaturated cyclic hydrocarbons containing 3 to 12 carbons, preferably 5 to 10 carbons and 1 or 2 double bonds. Exemplary cycloalkenyl groups include cyclobutenyl, cyclopentenyl, cyclohexenyl, cycloheptenyl, cyclooctenyl, cyclohexadienyl, and cycloheptadienyl. Optionally, said cycloalkenyl group may be substituted with one or substituents, such as those substituents disclosed for alkyl.

The term "Bicycloalkyl" as employed herein alone or as part of another group includes saturated bicyclic ring groups such as, without limitation, [3.3.0]bicyclooctane, [4.3.0]bicyclononane, [4.4.0]bicyclodecane (decalin), [2.2.2]bicyclooctane, and so forth.

The term "cycloalkenyl" as employed herein alone or as part of another group includes partially unsaturated carbocyclic radicals having three to twelve carbon atoms. Examples include, without limitation, cyclobutenyl, cyclopentenyl and cyclohexenyl.

The term "polycycloalkyl" as employed herein alone or as part of another group includes two or more cycloalkyl ring systems, as defined herein, wherein at least one carbon atom is a part of at least two separately identifiable ring systems. The polycycloalkyl group may contain bridging between two carbon atoms, for example, bicyclo[1.1.0]butyl, bicyclo [3.2.1]octyl, bicyclo[5.2.0]nonyl, tricycl[2.2.1.0.sup.1]heptyl, norbornyl and pinanyl. The polycycloalkyl group may contain one or more fused ring systems, for example, decalinyl (radical from decalin) and perhydroanthracenyl. The polycycloalkyl group may contain a spiro union, in which a single atom is the only common member of two rings, for example, spiro[3.4]octyl, spiro[3.3]heptyl and spiro[4.5]decyl.

The term "halogen" or "halo" as used herein alone or as part of another group refers to chlorine, bromine, fluorine, and iodine as well as $CF_3$.

The term "alkoxy" or "alkyloxy" as used herein alone or as part of another group, refers to an alkyl group, as defined herein, appended to a parent molecular moiety through an alkyl group, as defined herein.

The term "haloalkoxy" as used herein alone or as part of another group refers to alkoxy radicals, as defined herein, further substituted with one or more halo atoms, such as fluoro, chloro or bromo, to provide haloalkoxy radicals. Examples include, without limitation, fluoromethoxy, chloromethoxy, trifluoromethoxy, trifluoromethoxy, fluoroethoxy and fluoropropoxy.

The term "acyl" as employed herein by itself or part of another group, as defined herein, refers to an organic radical linked to a carbonyl

group; examples of acyl groups include a substituent group attached to a carbonyl, such as alkanoyl, alkenoyl, aroyl, aralkanoyl, heteroaroyl, cycloalkanoyl, cycloheteroalkanoyl and the like.

The term "cycloalkylalkyl", "arylalkyl", "cycloheteroalkyl", "bicycloalkylalkyl" or "heteroarylalkyl" as used herein alone or as part of another group, refers to a cycloalkyl, an aryl, a cyclohetero, a bicycloalkyl or heteroaryl group, as defined herein, appended to a parent molecular moiety through an alkyl group, as defined herein. Representative examples of arylalkyl include, but are not limited to, benzyl, 2-phenylethyl, 3-phenylpropyl, and the like.

The term "cycloheteroalkylalkyl" as used herein alone or as part of another group refers to a cycloheteroalkyl group as defined herein. linked through a C atom or heteroatom to a $(CH_2)_r$ chain, where "r" can be 1 to 10.

The term "polyhaloalkyl" as used herein alone or as part of another group refers to an "alkyl" group as defined above, having 2 to 9, preferably from 2 to 5, halo substituents, such as $CF_3CH_2$, $CF_3$ or $CF_3CF_2CH_2$.

The term "polyhaloalkoxy" as used herein refers to an "alkoxy" or "alkyloxy" group as defined above having 2 to 9, preferably from 2 to 5, halo substituents, such as $CF_3CH_2O$—, $CF_3O$— or $CF_3CF_2CH_2O$—.

The term "thiol" or "thio" as used herein alone or as part of another group, refers to (—S) or (—S—).

The term "alkylthio" or "arylalkylthio" refers to an alkyl group or and arylalkyl group, as defined herein, linked to a parent molecular moiety through a thiol group.

The term "alkylthioalkyl" or "arylalkylthioalkyl" refers to an alkylthio group or and arylalkylthio group, as defined herein, linked to a parent molecular moiety through an alkyl group.

The term "hydroxy" as used herein alone or as part of another group, refers to a —OH group.

The term "hydroxyalkyl" as used herein alone or as part of another group, refers to a hydroxyl group, as defined herein, appended to a parent molecular moiety through a alkyl group, as defined herein.

The term "cyano" as used herein alone or as part of another group, refers to a —CN group.

The term "nitro" as used herein, refers to a —$NO_2$ group.

The term "sulfinyl", whether used alone or linked to other terms such as alkylsulfinyl, denotes respectively divalent radicals —S(O)—.

The term "alkylsulfinyl " as used herein alone or as part of another group, refers to an alkyl group, as defined herein, appended to a parent molecular moiety through a sulfinyl group, as defined herein.

The term "sulfonyl" as used herein alone or as part of another group, refers to an $SO_2$ group.

The term "alkylsulfonyl" or "aminosulfonyl", as used herein, refer to an alkyl or amino group, as defined herein, appended to a parent molecular moiety through a sulfonyl group, as defined herein.

The term "amino" as employed herein, refers to an —$NH_3$ group or an amine linkage: —$NR_a$—, wherein Ra may be as described below in the definition for "substituted amino".

The term "substituted amino" as employed herein alone or as part of another group refers to amino substituted with one or two substituents. For example, $NR_aR_b$, wherein $R_a$ and $R_b$ may be the same or different and are, for example chosen from hydrogen, alkyl, cycloalkyl, alkenyl, cycloalkenyl, alkynyl, aryl, heteroaryl, heterocyclic, arylalkyl, heteroarylalkyl, cycloheteroalkyl, cycloheteroalkylalkyl, cycloalkylalkyl, haloalklyl, hydrooxyalkyl, alkoxyalkyl or thioalkyl. These substituents may optionally be further substituted with any of the alkyl substituents as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-lpiperazinyl, 4-arylalkyl-1-piperazinyl, 4-diarylalkyl-1-piperazinyl, 1-pyrrolindinyl, 1-piperidinyl, or 1-azepinyl, optionally substituted with alkyl, alkoxy, alkylthio, halo, triflouromethyl or hydroxyl.

The term "dialkylamino" as employed herein alone, or as part of another group, refers to a substituted amino group having two alkyl substituents. For example, $NR_aR_b$, wherein $R_a$ and $R_b$ are each an alkyl group, as defined herein.

The term "carbonyl" as used herein, refers to a —C(O)— group.

The term "aminocarbonyl", "alkylcarbonyl", "alkoxycarbonyl", "arylcarbonyl", "alkynylaminocarbonyl", "alkylaminocarbonyl" and "alkenylaminocarbonyl" as used herein, refer to an amino group, alkyl group, alkoxy group, aryl group, alkynylamino group, alkylamino group or an alkenylamino group, as defined herein, appended to a parent molecular moiety through a carbonyl group, as defined herein.

The term "heteroarylamino", "arylamino", "alkylamino", "alkylcarbonylamino", "arylcarbonylamino", "alkylsulfonylamino", "alkylaminocarbonylamino" or "alkoxycarbonylamino" as used herein, refers to a heteroaryl, aryl, alkyl, alkylcarbonyl, arylcarbonyl, alkylsulfonyl, alkylaminocarbonyl or alkoxycarbonyl group as defined herein, appended to a parent molecular moiety through an amino group, as defined herein.

The term "sulfonamido" refers to —$S(O)_2$—$NR_aR_b$, wherein Ra and Rb are as defined above for "substituted amino".

The term "alkylcarbonyloxy" as used herein, refers to an "alkyl-CO—O—" group, wherein alkyl is as defined above.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Substituted," as used herein, whether express or implied and whether preceded by "optionally" or not, means that any one or more hydrogen on the designated atom (C, N, etc.) is replaced with a selection from the indicated group, provided that the designated atom's normal valency is not exceeded, and that the substitution results in a stable compound. For instance, when a $CH_2$ is substituted by a keto substituent (=O), then 2 hydrogens on the atom are replaced. Combinations of substituents and/or variables are permissible only if such combinations result in stable compounds. Further, when more than one position in a given structure may be substituted with a substituent selected from a specified group, the substituents may be either the same or different at every position.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art. A comprehensive description of prodrugs and prodrug derivatives are described in:

a) *The Practice of Medicinal Chemistry,* Camille G. Wermuth et al., Ch 31, (Academic Press, 1996);

b) *Design of prodrugs,* edited by H. Bundgaard, (Elsevier, 1985); and c) *A Textbook of Drug Design and Development,* P. Krogsgaard-Larson and H. Bundgaard, eds., Ch. 5, pgs 113-191 (Harwood Academic Publishers, 1991). Said references are incorporated herein by reference.

The conditions, diseases and maladies collectively referred to as "diabetic complications" include retinopathy, neuropathy and nephropathy, erectile dysfunction, and other known complications of diabetes.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The term "other type of therapeutic agents" as employed herein includes, but is not limited to one or more antidiabetic agents (other than DPP-IV inhibitors of formula I), one or more anti-obesity agents, one or more anti-hypertensive agents, one or more anti-platelet agents, one or more anti-atherosclerotic agents and/or one or more lipid-lowering agents (including anti-atherosclerosis agents).

UTILITIES AND COMBINATIONS

A. Utilities

The compounds of the present invention possess activity as inhibitors of the dipeptidyl peptidase IV which is found in a variety of tissues, such as the intestine, liver, lung and kidney of mammals. Via the inhibition of dipeptidyl peptidase IV in vivo, the compounds of the present invention possess the ability to potentiate endogenous levels of GLP-1(7-36) and attenuate formation of its antagonist GLP-1(9-36).

Accordingly, the compounds of the present invention can be administered to mammals, preferably humans, for the treatment of a variety of conditions and disorders, including, but not limited to, treating or delaying the progression or onset of diabetes(preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis and hypertension. The compounds of the present invention may also be utilized to increase the blood levels of high density lipoprotein (HDL).

In addition, the conditions, diseases, and maladies collectively referenced to as "Syndrome X" or Metabolic Syndrome as detailed in Johannsson, *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

Other "therapeutic agent(s)" suitable for combination with the compound of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents, and appetite suppressants. Additional therapeutic agents suitable for combination with the compound of the present invention include agents for treating infertility, agents for treating polycystic ovary syndrome, agents for treating a growth disorder and/or frailty, an anti-arthritis agent, agents for preventing inhibiting allograft rejection in transplantation, agents for treating autoimmune disease, an anti-AIDS agent, agents for treating inflammatory bowel disease/syndrome, agents for treating anorexia nervosa and an anti-osteoporosis agent.

Examples of suitable anti-diabetic agents for use in combination with the compound of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, STLT2 inhibitors and other dipeptidyl peptidase IV (DPP4) inhibitors.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Examples of PPAR-alpha agonists, PPAR-gamma agonists and PPAR alpha/gamma dual agonists include muraglitizar, peliglitazar, AR-HO39242 (Astra/Zeneca), GW-409544 (Glaxo-Wellcome), GW-501516 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), WO 01/21602 and in U.S. Pat. No. 6,653,314, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable other DPP4 inhibitors include saxagliptin, those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540), 2-cyanopyrrolidides and 4-cyanopyrrolidides, as disclosed by Ashworth et al, Bioorg. & Med. Chem. Lett., Vol. 6, No.22, pp 1163-1166 and 2745-2748 (1996), the compounds disclosed in U.S. application Ser. No. 10/899641, WO 01/868603 and U.S. Pat. No. 6,395,767, employing dosages as set out in the above references.

Other suitable meglitinides include nateglinide (Novartis) or KAD1229 (PF/Kissei).

Examples of suitable anti-hyperglycemic agents for use in combination with the compound of the present invention include glucagon-like peptide-1 (GLP-1,) such as GLP-1(1-36) amide, GLP-1(7-36) amide, GLP-1(7-37) (as disclosed in U.S. Pat. No. 5,614,492), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671.

Examples of suitable hypolipidemic/lipid lowering agents for use in combination with the compound of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (e.g., CETP inhibitors, such as CP-529414 (Pfizer) and JTT-705

(Akros Pharma)), PPAR agonists (as described above) and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983 and 5,962,440.

The HMG CoA reductase inhibitors which may be employed in combination with one or more compound of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No.0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compound of the present invention.

The squalene synthetase inhibitors suitable for use herein include, but are not limited to, α-phosphono-sulfonates disclosed in U.S. Pat. No. 5,712,396, those disclosed by Biller et al., J. Med. Chem., 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination the compound of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination the compound of formula I include those disclosed in Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an up-regulator of LD2 receptor activity, such as MD-700 (Taisho Pharmaceutical Co. Ltd) and LY295427 (Eli Lilly).

Examples of suitable cholesterol absorption inhibitor for use in combination with the compound of the invention include SCH48461 (Schering-Plough), as well as those disclosed in Atherosclerosis 115, 45-63 (1995) and J. Med. Chem. 41, 973 (1998).

Examples of suitable ileal Na+/bile acid co-transporter inhibitors for use in combination with the compound of the invention include compounds as disclosed in Drugs of the Future, 24, 425-430 (1999).

The lipoxygenase inhibitors which may be employed in combination the compound of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compound of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compound of the present invention include a beta 3 adrenergic agonist, a lipase inhibitor, a serotonin (and dopamine) reuptake inhibitor, a thyroid receptor beta drug, 5HT2C agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonsist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

The beta 3 adrenergic agonists which may be optionally employed in combination with compound of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064.

Examples of lipase inhibitors which may be optionally employed in combination with compound of the present invention include orlistat or ATL-962 (Alizyme).

The serotonin (and dopoamine) reuptake inhibitor (or serotonin receptor agonists) which may be optionally employed in combination with a compound of the present invention may be BVT-933 (Biovitrum), sibutramine, topiramate (Johnson & Johnson) or axokine (Regeneron).

Examples of thyroid receptor beta compounds which may be optionally employed in combination with the compound of the present invention include thyroid receptor ligands, such as those disclosed in WO97/21993 (U. Cal SF), WO99/00353 (KaroBio) and GB98/284425 (KaroBio).

The monoamine reuptake inhibitors which may be optionally employed in combination with compound of the present invention include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The anorectic agent which may be optionally employed in combination with the compound of the present invention include topiramate (Johnson & Johnson), dexamphetamine, phentermine, phenylpropanolamine or mazindol.

The aforementioned patents and patent applications are incorporated herein by reference.

The above other therapeutic agents, when employed in combination with the compound of the present invention may be used, for example, in those amounts indicated in the Physician's Desk Reference, as in the patents set out above or as otherwise determined by one of ordinary skill in the art.

Where the compound of the invention are utilized in combination with one or more other therapeutic agent(s), either concurrently or sequentially, the following combination ratios and dosage ranges are preferred.

Where the other antidiabetic agent is a biguanide, the compound of formula I will be employed in a weight ratio to biguanide within the range from about 0.01:1 to about 100:1, preferably from about 0.1:1 to about 5:1.

The compound of formula I will be employed in a weight ratio to the glucosidase inhibitor within the range from about 0.01:1 to about 100:1, preferably from about 0.5:1 to about 50:1.

The compound of formula I will be employed in a weight ratio to the sulfonyl urea in the range from about 0.01:1 to about 100:1, preferably from about 0.2:1 to about 10:1.

The compound of formula I will be employed in a weight ratio to the thiazolidinedione in an amount within the range from about 0.01:1 to about 100:1, preferably from about 0.2:1 to about 10:1.

Where present, the thiazolidinedione anti-diabetic agent may be employed in amounts within the range from about 0.01 to about 2000 mg/day which may be administered in single or divided doses one to four times per day.

Optionally, the sulfonyl urea and thiazolidinedione may be incorporated in a single tablet with the compound of formula I in amounts of less than about 150 mg.

Where present, metformin or salt thereof may be employed in amounts within the range from about 500 to about 2000 mg per day which may be administered in single or divided doses one to four times daily.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The compound of formula I will be employed in a weight ratio to the meglitinide, PPAR-gamma agonist, PPAR-alpha/gamma dual agonist, aP2 inhibitor or other DPP4 inhibitor within the range from about 0.01:1 to about 100:1, preferably from about 0.2:1 to about 10:1.

The compound of formula I of the invention will be generally be employed in a weight ratio to the hypolipidemic agent (were present), within the range from about 500:1 to about 1:500, preferably from about 100:1 to about 1:100.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor in an amount within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

The squalene synthetase inhibitor may be employed in dosages in an amount within the range of from about 10 mg to about 2000 mg and preferably from about 25 mg to about 200 mg.

A preferred oral dosage form, such as tablets or capsules will contain the squalene synthetase inhibitor in an amount of from about 10 to about 500 mg, preferably from about 25 to about 200 mg.

The compound of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out a preferred method of the invention for treating any of the diseases disclosed herein, such as diabetes and related diseases, a pharmaceutical composition will be employed containing one or more of the compound of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compound can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 10 to about 500 mg of a compound of formula I. The dose for adults is preferably between 10 and 2,000 mg per day, which can be administered in a single dose or in the form of individual doses from 1-4 times per day.

A typical injectable preparation may be produced by aseptically placing 250 mg of compound of formula I into a vial, aseptically freeze-drying and sealing. For use, the contents of the vial are mixed with 2 mL of physiological saline, to produce an injectable preparation.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

DPP-4 inhibitory activity of the compounds of the present invention may be determined by use of an in vitro assay system which measures the degree in inhibition of DPP-4-mediated cleavage of an appropriate substrate or pseudosubstrate. Inhibition constants (Ki values) for the DPP-4 inhibitors of the invention may be determined by the method described in the experimental section below.

Cloning, Expression and Purification of Human DPP-4

To generate human DPP-4, PCR (Red-tag polymerase, Sigma) was performed on Human cDNA from placenta (Clontech) using two primers, ACGCCGACGATGAAGACA (SEQ. ID NO:1) and AGGTAAAGAGAAACATTGTT (SEQ ID NO:2),based on the nucleotide sequence of the human clone (accession number M74777). PCR products were cloned into the pcDN4/HisMax TOPO vector (Invitrogene). For stable transfection of CHO-DG44 cells, DPP4 was rePCRed using primers GGTACCAGCGCAGAGGCTT (SEQ. ID NO:3) and CTCGAGCTAAGGTAAAGAGAAACATTG (SEQ. ID NO:4) to generate KpnI and XhoI sites. The KpnI and XhoI sites were used to extract the N-terminal His tagged gene. The His tag, which could be cleaved and removed by Enterokinase, was included to allow purification using the TALON affinity column. The gene was then ligated into the KpnI and XhoI sites of the pD16 vector for stable transfection. Stable cell lines were generated by transfecting the expression vector into Chinese hamster ovary (CHO-DG44) cells using electroporation. The CHO-DG44 cell line was grown in PFCHO media supplemented with HT (glycine, hypoxanthine and thymidine, Invitrogene), glutamine and Recombulin (ICN). Then $1 \times 10^7$ cells/ml were collected, transfected with 60 µg of DNA using electroporation at 300V, and then transferred to a T75 flask. On the third day following transfection, the HT supplement was removed and selection was initiated with methotrexate (MTX, 10 nM, ICN). After a further 10 days the cells were plated into individual wells of 96 well plates. Every 10 days the concentration of MTX was increased two to three fold, up to a maximum of 400 nM. Final stable cell line selection was based on yield and activity of the expressed protein.

An attempt to purify recombinant DPP-4 using Talon resin was not efficient, resulting in small yields, with most of the DPP activity passing through the column. Therefore, protein was further purified using conventional anion exchange (Sepharose Q), gel filtration (S-200) and high resolution MonoQ columns. The final protein yielded a single band on SDS-PAGE gels. Amino acid sequence analysis indicated two populations of DPP-4 in the sample. One portion of the protein had 27 amino acids truncated from the N-terminus, while the other was lacking the N-terminal 37 amino acids. This suggests that during isolation the entire transmembrane domain (including His tag) is removed by proteases present in the CHO cells. Total protein concentration was measured using the Bradford dye method and the amount of the active DPP-4 was determined by titrating the enzyme with a previously characterized inhibitor (Ki=0.4 nM). No biphasic behavior was observed during inhibition or catalysis, suggesting that both protein populations are functionally identical.

DPP-4 Inhibition Assays.

Inhibition of human DPP-4 activity was measured under steady-state conditions by following the absorbance increase at 405 nm upon the cleavage of the pseudosubstrate, Gly-Pro-pNA. Assays were performed in 96-well plates using a Thermomax plate reader. Typically reactions contained 100 µl of ATE buffer (100 mM Aces, 52 mM Tris, 52 mM ethanolamine, pH 7.4), 0.45 nM enzyme, either 120 or 1000 μM of substrate (S<Km and S>Km, Km=180 μM) and variable concentration of the inhibitor. To ensure steady-state conditions for slow-binding inhibitors, enzyme was preincubated with the compound for 40 minutes prior to substrate addition, to initiate the reaction. All serial inhibitor dilutions were in DMSO and final solvent concentration did not exceed 1%.

Inhibitor potency was evaluated by fitting inhibition data to the binding isotherm:

$$\frac{vi}{v} = \frac{\text{Range}}{1 + \left(\frac{I}{IC_{50}}\right)^n} + \text{Background} \quad (1)$$

where vi is the initial reaction velocity at different concentrations of inhibitor I; v is the control velocity in the absence of inhibitor, range is the difference between the uninhibited velocity and background; background is the rate of spontaneous substrate hydrolysis in the absent of enzyme, n is the Hill coefficient.

Calculated $IC_{50}$ at each substrate concentration were converted to Ki assuming competitive inhibition according to:

$$Ki = \frac{IC_{50}}{\left(1 + \frac{S}{Km}\right)} \quad (2)$$

All inhibitors were competitive as judged by a very good agreement of Ki values obtained from the assays at high and low substrate concentrations. In cases where $IC_{50}$ at the low substrate concentration was close to the enzyme concentration used in the assay, the data were fit to the Morrison equation[1], to account for the depletion of the free inhibitor:

[1]Morrison, J F, Walsh, C T. Advances in Enzymology. 61 (1988), 201-206.

$$\frac{vi}{v0} = 1 - \frac{(E+I+IC_{50}) - \sqrt{(E+I+IC_{50})^2 - 4EI}}{2E} \quad (3)$$

where vi and vo are the steady state velocities measured in the presence and absence of inhibitor, E enzyme concentration.

Each $IC_{50}$ was further refined to Ki, to account for the substrate concentration in the assay using equation (2).

ABBREVIATIONS

The following abbreviations are employed in the Examples and elsewhere herein:
Ph=phenyl
Bn=benzyl
i-Bu=iso-butyl
Me=methyl
Et=ethyl
Pr=propyl
Bu=butyl
TMS=trimethylsilyl
FMOC=fluorenylmethoxycarbonyl
Boc or BOC=tert-butoxycarbonyl
Cbz=carbobenzyloxy or carbobenzoxy or benzyloxycarbonyl
HOAc or AcOH=acetic acid
DMF=N,N-dimethylformamide
DMSO=dimethylsulfoxide
EtOAc=ethyl acetate
THF=tetrahydrofuran
TFA=trifluoroacetic acid
$Et_2NH$=diethylamine
NMM=N-methyl morpholine
n-BuLi=n-butyllithium
Pd/C=palladium on carbon
$PtO_2$=platinum oxide
TEA=triethylamine
min=minute(s)
h or hr=hour(s)
L=liter
mL=milliliter
μL=microliter
g=gram(s)
mg=milligram(s)
mol=mole(s)
mmol=millimole(s)
meq=milliequivalent
rt=room temperature
sat or sat'd=saturated
aq.=aqueous
TLC=thin layer chromatography
$t_R$=retention time
mp=melting point
HPLC=high performance liquid chromatography
LC/MS=high performance liquid chromatography/mass spectrometry
MS or Mass Spec=mass spectrometry
NMR=nuclear magnetic resonance
EDCI or EDAC=3-ethyl-3'-(dimethylamino)propyl-carbodiimide hydrochloride (or 1-[(3-(dimethyl)amino)propyl])-3-ethylcarbodiimide hydrochloride)
HOBT or $HOBT.H_2O$=1-hydroxybenzotriazole hydrate
HOAT=1-hydroxy-7-azabenzotriazole
PyBOP reagent=benzotriazol-1-yloxy-tripyrrolidino phosphonium hexafluorophosphate
equiv=equivalent(s)
UCT=United Chemical Technologies, Inc.; Bristol, Pa.

EXAMPLES

The following examples are provided to describe the invention in further detail. These examples, which set forth the best mode presently contemplated for carrying out the invention, are intended to illustrate and not to limit the invention.

In general, preferred compounds of the present invention, such as the compounds disclosed in the following examples, have been identified to inhibit the catalytic activity of dipeptidyl peptidase IV at concentrations equivalent to, or more potently than, 10 μM, preferably 5 μM, more preferably 3 μM, thereby corroborating the utility of the compounds of the present invention as effective inhibitors dipeptidyl peptidase IV. Potencies can be calculated and expressed as either inhibition constants (Ki values) or as IC50 (inhibitory concentra-

Example 1

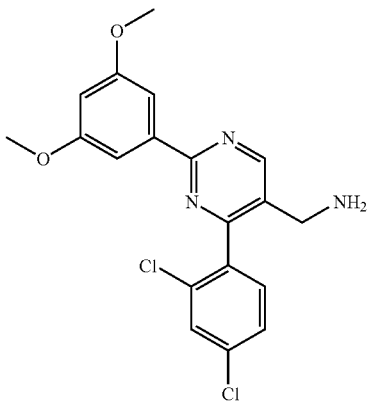

Example 1

Step 1. 3-(2,4-Dichlorophenyl)-3-oxopropanenitrile

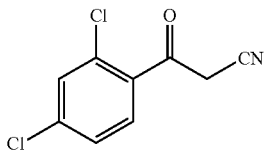

To a stirred solution of acetonitrile (2.0 mL, 38.2 mmol) in THF (50 mL) at −78° C. was added ″BuLi (1.81 M in hexane, 16 mL, 28.7 mmol). The resulting slurry was kept at −78° C. for 15 min and 2,4-dichlorobenzoyl chloride (2.0 g, 9.55 mmol) was added dropwise to the acetonitrile anion. After 40 min, the reaction was quenched by addition of saturated NH$_4$Cl (30 mL). THF was removed under reduced pressure and the suspension was filtered. The solid was washed with H$_2$O (100 mL) and dried to give 3-(2,4-dichlorophenyl)-3-oxopropanenitrile (2.0 g, 98%, >95% purity) as a light yellow solid.

$^1$H NMR (400 MHz, CDCl$_3$) 7.64 (d, J=8.32 Hz, 1H), 7.52 (d, J=1.76 Hz, 1H), 7.41 (dd, J=1.76, 8.32 Hz, 1H), 4.13 (s, 2H).

HPLC Phenomenex LUNA C-18 4.6×50 mm, 0 to 100% B over 4 minutes, 1 minutes hold time, A=90% water, 10% methanol, 0.2% phosphoric acid, B=10% water, 90% methanol, 0.2% phosphoric acid, RT=2.73 min, 95.5% homogeneity index.

LCMS: Anal. Calcd. for C$_9$H$_5$Cl$_2$NO 212.97 found: 211.89 (M−H)$^-$.

Example 1

Step 2. 2-(2,4-Dichlorobenzoyl)-3-(dimethylamino) acrylonitrile

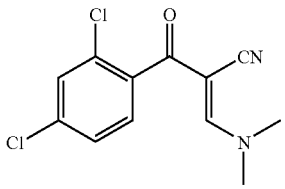

To a stirred solution of step 1 nitrile (1.74 g, 8.13 mmol) in toluene (50 mL) was added dimethylformamide dimethylacetal (1.35 mL, 10.16 mmol). The resulting brown solution was heated to 50° C. for 1 hr. The solvent was removed under reduced pressure and the residue was diluted with CH$_2$Cl$_2$ (50 mL). The organic layer was washed with saturated NaHCO$_3$ solution (50 mL) and brine (50 mL), dried (MgSO$_4$), filtered and concentrated under reduced pressure to give the crude product as a brown oil. Purification of the crude product by flash chromatography (silica gel, 40% EtOAc/hexane) afforded 2-(2,4-dichlorobenzoyl)-3-(dimethylamino)acrylonitrile (1.5 g, 69%) as a light brown oil.

$^1$H NMR (400 MHz, CDCl$_3$) 7.43 (s, 1H), 7.30 (s, 2H), 3.48 (s, 3H), 3.32 (s, 3H).

Example 1

Step 3. 4-(2,4-Dichlorophenyl)-2-(3,5-dimethoxyphenyl)pyrimidine-5-carbonitrile

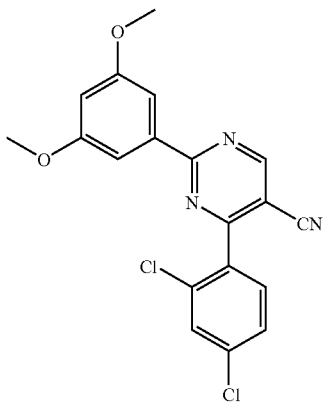

To a stirred solution of Step 2 acrylonitrile (1.5 g, 5.6 mmol) and 3,5-dimethoxybenzamidine hydrochloride (1.2 g, 5.6 mmol) in MeOH (30 mL) was added NaOMe (25% in MeOH, 2.56 mL, 11.2 mmol). The reaction was heated to reflux for 5 hr. Additional NaOMe (25% in MeOH, 2.56 mL, 11.2 mmol) was added and was kept for 16 hr. The reaction was cooled to ambient temperature and quenched by addition of H$_2$O (50 mL). The reaction was filtered and the solid was washed with MeOH (40 mL) to give 4-(2,4-dichlorophenyl)-2-(3,5-dimethoxyphenyl)pyrimidine-5-carbonitrile (960 mg, 38.4%) as a white solid.

¹H NMR (400 MHz, CDCl₃) 9.10 (s, 1H), 7.71 (d, J=2.2 Hz, 2H), 7.62 (d, J=1.75 Hz, 1H), 7.51 (d, J=7.78 Hz, 1H), 7.47 (dd, J=1.75, 7.76 Hz, 1H), 6.68 (t, J=2.1 Hz, 1H), 3.88 (s, 6H).

¹³H NMR (400 MHz, CDCl₃) 166.44, 165.67, 161.25, 160.79, 137.63, 137.59, 133.62, 133.31, 131.66, 130.49, 127.71, 114.93, 107.07, 106.89, 105.64, 55.65.

HPLC Phenomenex LUNA C-18 4.6×50 mm, 0 to 100% B over 4 minutes, 1 minutes hold time, A=90% water, 10% methanol, 0.2% phosphoric acid, B=10% water, 90% methanol, 0.2% phosphoric acid, RT=4.14 min.

LCMS: Anal. Calcd. for $C_{19}H_{13}C_{12}N_3O_2$ 385.04 found: 386.15 (M+H)⁺.

Example 1

Step 4. (4-(2,4-Dichlorophenyl)-2-(3,5-dimethoxyphenyl)pyrimidin-5-yl)methanamine

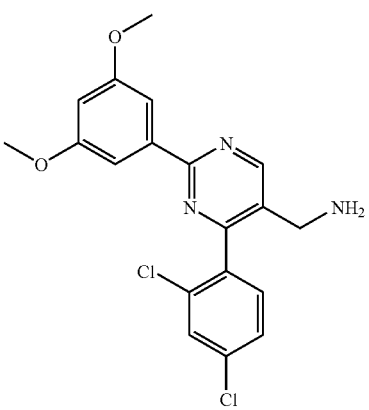

To a stirred solution of Step 3 carbonitrile (35 mg, 0.09 mmol) in THF (2 mL) and H₂O (1 mL) was added CoCl₂.6H₂O (20 mg, 0.09 mmol) followed by NaBH₄ (17 mg, 0.45 mmol) in H₂O (0.5 mL). A black precipitate formed immediately with gas evolution. After 30 min, the reaction was filtered and diluted with CH₂Cl₂ (6 mL). The organic layer was washed with saturated NaHCO₃ solution (5 mL) and brine (5 mL), dried (MgSO₄), filtered and concentrated under reduced pressure to give the crude product as a yellow oil. Purification of the crude product by reverse-phase preparative HPLC provided (4-(2,4-dichlorophenyl)-2-(3,5-dimethoxyphenyl)pyrimidin-5-yl)methanamine, TFA salt (20 mg, 44%) as a light yellow solid.

¹H NMR (400 MHz, CD₃OD) 9.06 (s, 1H), 7.41 (s, 1H), 7.64 (d, J=2.64 Hz, 2H), 7.61 (dd, J=1.76, 7.75 Hz, 1H), 7.55 (d, J=7.76 Hz, 1H), 6.66 (d, J=1.80 Hz, 1H), 4.02 (br s, 2H), 3.84 (s, 6H).

HPLC Phenomenex LUNA C-18 4.6×50 mm, 0 to 100% B over 4 minutes, 1 minutes hold time, A=90% water, 10% methanol, 0.1% trifluoroacetic acid, B=10% water, 90% methanol, 0.1% trifluoroacetic acid, RT=3.19 min, 97% homogeneity index.

HRMS: Anal. Calcd. for $C_{19}H_{17}C_{12}N_3O_2$ 390.0776 found: 390.0778 (M+H)⁺.

Example 2

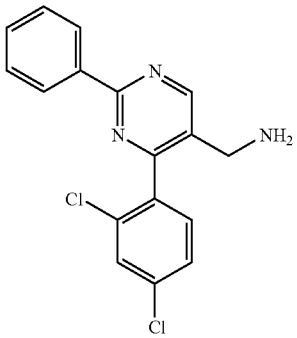

(4-(2,4-Dichlorophenyl)-2-phenylpyrimidin-5-yl)methanamine, TFA salt was prepared by the methods described in Example 1, Step 3 and Step 4 using Example 1, Step 2 acrylonitrile and benzamidine hydrochloride.

¹H NMR (400 MHz, CD₃OD) 9.07 (s, 1H), 8.46 (dd, J=1.76, 8.36 Hz, 2H), 7.76 (d, J=1.44 Hz, 1H), 7.47-7.63 (m, 5H), 4.16 (br s, 2H).

HPLC Phenomenex LUNA C-18 4.6×50 mm, 0 to 100% B over 4 minutes, 1 minutes hold time, A=90% water, 10% methanol, 0.2% phosphoric acid, B=10% water, 90% methanol, 0.2% phosphoric acid, RT=2.82 min, 98% homogeneity index.

LCMS: Anal. Calcd. for $C_{17}H_{13}C_{12}N_3$ 329.05 found: 330.14 (M+H)⁺.

Example 3

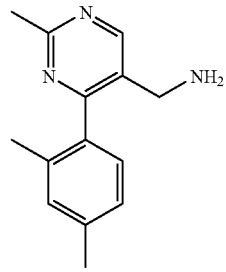

(4-(2,4-Dimethylphenyl)-2-methylpyrimidin-5-yl)methanamine, TFA salt was prepared by the methods described in Example 1, using 2,4-dimethylbenzaldehyde for Step 1 and acetamidine for Step 3.

¹H NMR (400 MHz, CD₃OD) 8.79 (s, 1H), 7.13 (s, 1H), 7.06 (d, J=8.8 Hz, 1H), 7.03 (d, J=8.8 Hz, 1H), 3.91 (s, 2H), 2.63 (s, 3H), 2.27 (s, 3H), 2.00 (s, 3H).

HPLC Phenomenex LUNA C-18 4.6×50 mm, 0 to 100% B over 4 minutes, 1 minutes hold time, A=90% water, 10% methanol, 0.2% phosphoric acid, B=10% water, 90% methanol, 0.2% phosphoric acid, RT=2.64 min, 95% homogeneity index.

HRMS: Anal. Calcd. for $C_{14}H_{17}N_3$ 228.1501 found: 228.1491 (M+H)$^+$.

Example 4

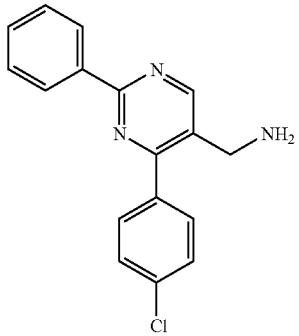

(4-(4-Chlorophenyl)-2-phenylpyrimidin-5-yl)methanamine, TFA salt was prepared by the methods described in Example 1 using 4-chlorobenzoyl chloride for Step 1 and benzamidine hydrochloride for Step 3.

$^1$H NMR (400 MHz, CD$_3$OD) 8.93 (s, 1H), 8.40 (dd, J=1.76, 7.88 Hz, 2H), 7.63 (d, J=8.32 Hz, 2H), 7.52 (d, J=8.80 Hz, 2H), 7.42 (m, 1H), 7.41 (d, J=7.04 Hz, 2H), 4.26 (s, 2H).

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=5.05 min, 96% homogeneity index.

HRMS: Anal. Calcd. for $C_{17}H_{15}ClN_3$ 296.0955 found: 296.0947 (M+H)$^+$.

Example 5

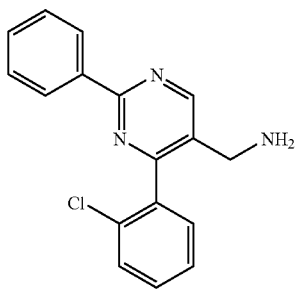

(4-(2-Chlorophenyl)-2-phenylpyrimidin-5-yl)methanamine, TFA salt was prepared by the methods described in Example 1 using 2-chlorobenzoyl chloride for Step 1 and benzamidine hydrochloride for Step 3.

$^1$H NMR (400 MHz, CD$_3$OD) 9.08 (s, 1H), 8.47 (dd, J=1.32, 7.48 Hz, 2H), 7.47-7.67 (m, 7H), 4.01 (br s, 2H).

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=4.92 min, 95% homogeneity index.

HRMS: Anal. Calcd. for $C_{17}H_{15}ClN_3$ 296.0955 found: 296.0945 (M+H)$^+$.

Example 6

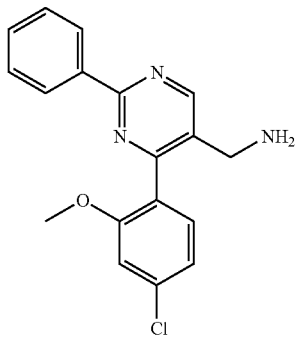

(4-(4-Chloro-2-methoxyphenyl)-2-phenylpyrimidin-5-yl)methanamine, TFA salt was prepared by the methods described in Example 1 using 2-methoxy-4-chlorobenzoyl chloride for Step 1 and benzamidine hydrochloride for Step 3.

$^1$H NMR (400 MHz, CD$_3$OD) 8.96 (s, 1H), 8.44 (dd, J=1.76, 7.92 Hz, 2H), 7.51 (m, 4H), 7.27 (d, J=1.76 Hz, 1H), 7.22 (dd, J=1.80, 7.75 Hz, 1H), 4.08 (s, 2H), 3.88 (s, 3H).

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=5.49 min, 98% homogeneity index.

HRMS: Anal. Calcd. for $C_{18}H_{17}ClN_3O$ 326.1060 found: 326.1048 (M+H)$^+$.

Example 7

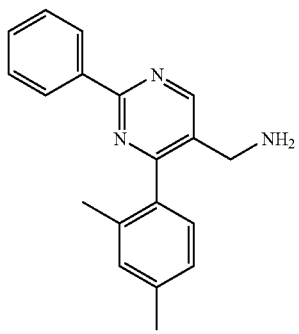

(4-(2,4-Dimethylphenyl)-2-phenylpyrimidin-5-yl)methanamine, TFA salt was prepared by the methods described in Example 1 using 2,4-dimethylbenzoyl chloride for Step 1 and benzamidine hydrochloride for Step 3.

$^1$H NMR (400 MHz, CD$_3$OD) 9.14 (s, 1H), 8.43 (dd, J=1.75, 7.60 Hz, 2H), 7.53 (m, 3H), 7.26 (m, 3H), 4.13 (s, 2H), 2.42 (s, 3H), 2.14 (s, 3H).

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=5.39 min, 99% homogeneity index.

HRMS: Anal. Calcd. for $C_{19}H_{20}N_3$ 290.1657 found: 290.1643 $(M+H)^+$.

Example 8

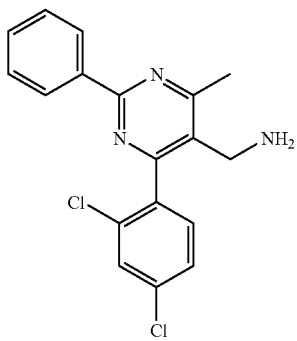

Example 8

Step 1. Methyl 2-(2,4-dichlorobenzylidene)-3-oxobutanoate

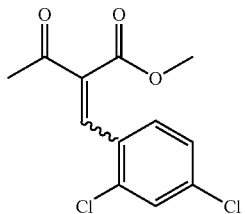

To a stirred solution of methyl acetoacetate (345 mg, 2.97 mmol) and 2,4-dichlorobenzaldehyde (500 mg, 2.86 mmol) in 2-propanol (5 mL) was added AcOH (7 mg, 0.11 mmol) and dimethylamine (0.06 mL, 2M in THF, 0.11 mmol). The reaction was heated to 40° C. for 4 hrs followed by cooling to ambient temperature for 15 hrs. The reaction was concentrated and purified by flash chromatography (silica gel, 30% EtOAc/hexane) to give methyl 2-(2,4-dichlorobenzylidene)-3-oxobutanoate as a mixture of two isomers (colorless oil, 610 mg, 78%).

$^1$H NMR (400 MHz, CDCl$_3$) Fast eluting isomer: 7.86 (s, 1H), 7.45 (d, J=2.2 Hz, 1H), 7.25 (d, J=6.8 Hz, 1H), 7.21 (dd, J=2.2, 7.0 Hz, 1H), 3.85 (s, 3H), 2.24 (s, 3H). Slow eluting isomer: 7.78 (s, 1H), 7.45 (d, J=2.2 Hz, 1H), 7.34 (d, J=7.0 Hz, 1H), 7.25 (dd, J=2.2, 7.0 Hz, 1H), 3.73 (s, 3H), 2.44 (s, 3H).

Example 8

Step 2. Methyl 4-(2,4-dichlorophenyl)-6-methyl-2-phenyl-1,4-dihydropyrimidine-5-carboxylate

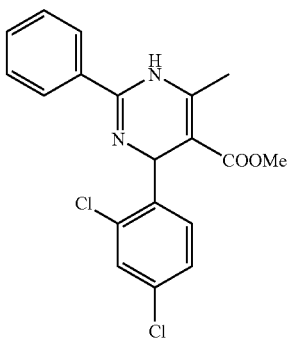

To a stirred solution of methyl 2-(2,4-dichlorobenzylidene)-3-oxobutanoate (480 mg, 1.8 mmol) and benzamidine HCl salt (275 mg, 1.8 mmol) in DMF (6 mL) was added NaOAc (144 mg, 1.8 mmol). The reaction was heated to 60° C. for 3 days and was quenched by 1N HCl (10 mL). The reaction was diluted with EtOAc (10 mL) and the organic layer was washed with 1N HCl, saturated NH4Cl solution (10 mL) and brine (10 mL), dried (MgSO$_4$), filtered and concentrated under reduced pressure to give the crude product as a yellow oil (600 mg). The crude reaction product was moved onto next step without further purification.

LCMS: Anal. Calcd. for $C_{19}H_{16}Cl_2N_2O_2$ 374.06 found: 375.00 $(M+H)^+$.

Example 8

Step 3. Methyl 4-(2,4-dichlorophenyl)-6-methyl-2-phenylpyrimidine-5-carboxylate

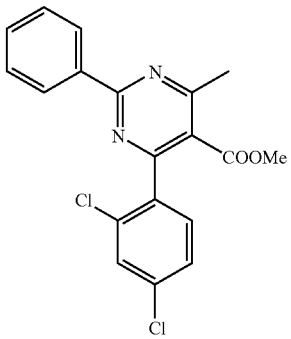

To a stirred solution of methyl 4-(2,4-dichlorophenyl)-6-methyl-2-phenyl-1,4-dihydropyrimidine-5-carboxylate (600 mg, 1.76 mmol) in PhCH$_3$ (6 mL) was added MnO$_2$ (227 mg, 2.64 mmol) and the reaction was heated to 95° C. for 14 hrs. The reaction was filtered through a pad of celite, concentrated under reduced pressure, and purified by flash chromatography (silica gel, 30% EtOAc/hexane) to give methyl 4-(2,4-dichlorophenyl)-6-methyl-2-phenylpyrimidine-5-carboxylate (150 mg, 23% for 2 steps) and 4-(2,4-dichlorophenyl)-6-methyl-2-phenylpyrimidine-5-carboxylic acid (100 mg, 15% for 2 steps).

$^1$H NMR (400 MHz, CDCl$_3$) 8.44 (dd, J=1.3, 7.6 Hz, 2H), 7.38-7.47 (m, 4H), 7.30 (d, J=1.3 Hz, 2H), 3.62 (s, 3H), 2.71 (s, 3H).

For acid $^1$H NMR (400 MHz, CDCl$_3$/CD$_3$OD) 8.04 (dd, J=1.3, 7.9 Hz, 2H), 7.41-7.57 (m, 3H), 7.37 (s, 1H), 7.26 (d, J=7.9 Hz, 2H), 2.48 (s, 3H).

HPLC Phenomenex LUNA C-18 4.6×50 mm, 0 to 100% B over 4 minutes, 1 minutes hold time, A=90% water, 10% methanol, 0.2% phosphoric acid, B=10% water, 90% methanol, 0.2% phosphoric acid, RT=3.63 min, 90% homogeneity index.

Example 8

Step 4. (4-(2,4-Dichlorophenyl)-6-methyl-2-phenylpyrimidin-5-yl)methanol

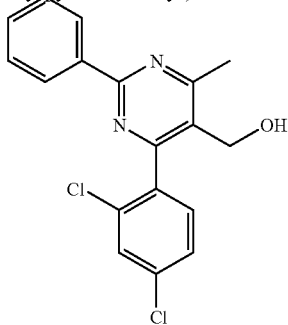

To a stirred solution of 4-(2,4-dichlorophenyl)-6-methyl-2-phenylpyrimidine-5-carboxylate (75 mg, 0.2 mmol) in THF (6 mL) was added DIBAL (0.4 mL, 1.5 M in PhCH$_3$, 0.6 mmol). The reaction was kept for 1 hr and was quenched by saturated aqueous potassium sodium tartrate solution (5 mL). The reaction was diluted with EtOAc (10 mL) and the organic layer was washed with 1N NaOH (10 mL), saturated Na$_2$CO$_3$ solution (10 mL) and brine (10 mL), dried (MgSO$_4$), filtered and concentrated under reduced pressure to give the crude product as a white solid (75 mg). The crude reaction product was moved onto next step without further purification.

$^1$H NMR (400 MHz, CDCl$_3$) 8.36 (dd, J=1.2, 7.5 Hz, 2H), 7.47 (s, 1H), 7.39 (m, 3H), 7.30 (dd, J=2.6, 8.0 Hz, 2H), 4.52 (br s, 1H), 4.42 (br s, 1H), 2.72 (s, 3H).

Example 8

Step 5. 4-(2,4-Dichlorophenyl)-6-methyl-2-phenylpyrimidine-5-carbaldehyde

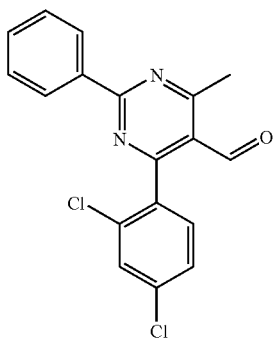

To a stirred solution of (4-(2,4-dichlorophenyl)-6-methyl-2-phenylpyrimidin-5-yl)methanol (75 mg, 0.2 mmol) in CH$_2$Cl$_2$ (6 mL) was added Dess-Martin periodinane (102 mg, 0.24 mmol). The reaction was kept for 2 hrs and was diluted with EtOAc (10 mL). The organic layer was washed with saturated NaHCO$_3$ solution (10 mL), and brine (10 mL), dried (MgSO$_4$), filtered and concentrated under reduced pressure to give the crude product as a white solid (75 mg). The crude product was purified by flash chromatography (silica gel, 30% EtOAc/hexane) to give 4-(2,4-dichlorophenyl)-6-methyl-2-phenylpyrimidine-5-carbaldehyde (65 mg, 91% for 2 steps) as a white solid.

$^1$H NMR (400 MHz, CDCl$_3$) 9.90 (s, 1H), 8.47 (dd, J=1.8, 8.4 Hz, 2H), 7.37-7.49 (m, 6H), 2.88 (s, 3H).

Example 8

Step 5. 4-(2,4-Dichlorophenyl)-6-methyl-2-phenylpyrimidine-5-carbaldehyde oxime

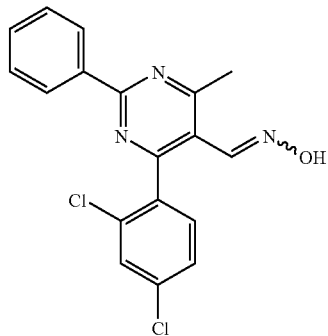

To a stirred solution of 4-(2,4-dichlorophenyl)-6-methyl-2-phenylpyrimidine-5-carbaldehyde (24 mg, 0.07 mmol) in EtOH (4 mL) was added NH$_2$OH.HCl (10 mg, 0.14 mmol) and Et$_3$N (50 μL). The reaction was heated to 70° C. for 3 hrs and was concentrated under reduced pressure. The residue was dissolved in EtOAc (10 mL) and the organic layer was washed by saturated NH$_4$Cl solution (10 mL) and brine, dried (MgSO$_4$), filtered and concentrated under reduced pressure to give the crude product as a white solid (24 mg). The crude reaction product was moved onto next step without further purification.

HPLC Phenomenex LUNA C-18 4.6×50 mm, 0 to 100% B over 4 minutes, 1 minutes hold time, A=90% water, 10% methanol, 0.1% trifluoroacetic acid, B=10% water, 90% methanol, 0.1% trifluoroacetic acid, RT=4.09 min, 95% homogeneity index.

LCMS: Anal. Calcd. for C$_{18}$H$_{13}$C$_{12}$N$_3$O 357.04 found: 357.97 (M+H)$^+$.

Example 8

Step 5. (4-(2,4-Dichlorophenyl)-6-methyl-2-phenylpyrimidin-5-yl)methanamine

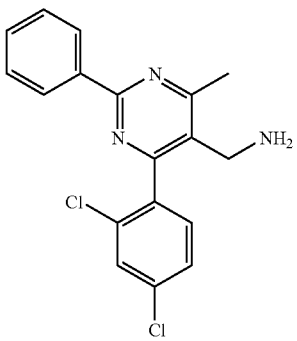

To a stirred solution 4-(2,4-dichlorophenyl)-6-methyl-2-phenylpyrimidine-5-carbaldehyde oxime (24 mg, 0.07 mmol) in EtOH (4 mL) was added Zn (14 mg, 0.21 mmol), NH$_4$OAc (16 mg, 0.21 mmol) and NH$_4$OH (30 µL, 28% in H$_2$O, 0.21 mmol). The reaction was heated to 78° C. for 15 hrs. Additional 3 eqs of Zn, NH$_4$OAc, NH$_4$OH were added and after 3 hrs, the reaction was concentrated under reduced pressure and diluted with EtOAc (10 mL). The organic layer was washed by saturated NaHCO$_3$ solution (10 mL) and brine, dried (MgSO$_4$), filtered and concentrated under reduced pressure to give the crude product. The crude product was purified by reverse-phase preparative HPLC to provide (4-(2,4-dichlorophenyl)-6-methyl-2-phenylpyrimidin-5-yl)methanamine, TFA salt (20 mg, 63% for 2 steps) as a light yellow solid.

$^1$H NMR (400 MHz, CD$_3$OD) 8.44 (dd, J=1.6, 8.4 Hz, 2H), 7.72 (d, J=1.3 Hz, 1H), 7.46-7.62 (m, 5H), 4.27 (d, J=14.5 Hz, 1H), 4.00 (d, J=14.5 Hz, 1H), 2.82 (s, 3H).

HPLC Phenomenex LUNA C-18 4.6×50 mm, 0 to 100% B over 4 minutes, 1 minutes hold time, A=90% water, 10% methanol, 0.2% phosphoric acid, B=10% water, 90% methanol, 0.2% phosphoric acid, RT=2.83 min, 99% homogeneity index.

LCMS: Anal. Calcd. for C$_{18}$H$_{15}$Cl$_2$N$_3$ 343.06 found: 343.99 (M+H)$^+$.

HRMS: Anal. Calcd. for C$_{18}$H$_{16}$Cl$_2$N$_3$ 344.0721 found: 344.0728 (M+H)$^+$.

Example 9

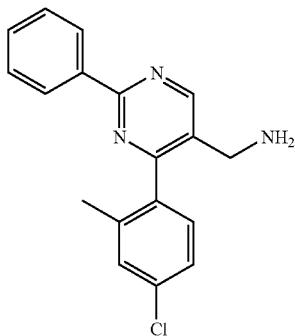

Example 9

Step 1. (4-Chloro-2-phenylpyrimidin-5-yl)methanol

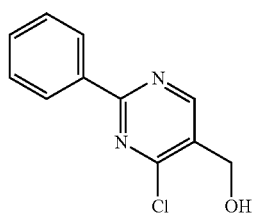

To a stirred solution of methyl 4-chloro-2-phenylpyrimidine-5-carboxylate (300 mg, 1.14 mmol) in CH$_2$Cl$_2$ (15 mL) at -78° C. was added DIBAL (1.5 M in PhCH$_3$, 1.5 mL, 2.28 mmol). The reaction was kept for 2 hrs and was quenched by saturated aqueous potassium sodium tartrate solution (10 mL). The reaction was diluted with EtOAc (15 mL) and the organic layer was washed with 1 N NaOH (10 mL), saturated Na$_2$CO$_3$ solution (10 mL) and brine (10 mL), dried (MgSO$_4$), filtered and concentrated under reduced pressure to give the crude product as a yellow solid (242 mg). The crude reaction product was moved onto next step without further purification.

$^1$H NMR (400 MHz, CD$_3$OD) 8.73 (s, 1H), 8.30 (d, J=1.3, 6.2 Hz, 2H), 7.38-7.41 (m, 3H), 4.64 (s, 2H).

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=6.17 min, 95% homogeneity index.

LCMS: Anal. Calcd. for C$_{11}$H$_9$ClN$_2$O 220.04 found: 221.04 (M+H)$^+$.

Example 9

Step 2.
4-Chloro-2-phenylpyrimidine-5-carbaldehyde

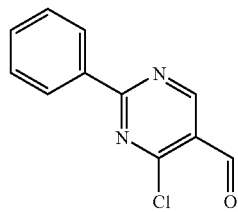

To a stirred (4-chloro-2-phenylpyrimidin-5-yl)methanol (242 mg, 1.10 mmol) in CH$_2$Cl$_2$ (11 mL) was added Dess-Martin periodinane (553 mg, 1.43 mmol). The reaction was kept for 2 hrs and was diluted with EtOAc (10 mL). The organic layer was washed with saturated NaHCO$_3$ solution (10 mL), and brine (10 mL), dried (MgSO$_4$), filtered and concentrated under reduced pressure to give the crude product as a white solid (250 mg). The crude product was purified by flash chromatography (silica gel, 20% EtOAc/hexane) to give 4-chloro-2-phenylpyrimidine-5-carbaldehyde (205 mg, 82% for 2 steps) as a white solid.

$^1$H NMR (400 MHz, CDCl$_3$) 10.43 (s, 1H), 9.12 (s, 1H), 8.51 (dd, J=1.4, 6.2 Hz, 2H), 7.48-7.59 (m, 3H).

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=6.60 min, 99% homogeneity index.

LCMS: Anal. Calcd. for C$_{11}$H$_7$ClN$_2$O 218.02 found: 219.06 (M+H)$^+$.

Example 9

Step 3. 4-(4-Chloro-2-methylphenyl)-2-phenylpyrimidine-5-carbaldehyde

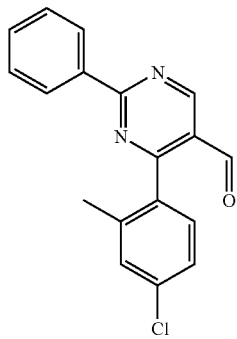

To a stirred solution of 4-chloro-2-phenylpyrimidine-5-carbaldehyde (50 mg, 0.23 mmol) and 4-chloro-o-toluene boronic acid (48 mg, 0.29 mmol) in dioxane (1 mL) and H$_2$O (0.5 mL) was added Pd(PPh$_3$)$_4$ (26.5 mg, 0.02 mmol), K$_2$CO$_3$ (126.5 mg, 0.92 mmol). The reaction was heated to 85° C. for 6 hrs. After concentration under reduced pressure, the residue was diluted with EtOAc (10 mL) and the organic layer was washed with saturated NH$_4$Cl solution (10 mL), and brine (10 mL), dried (MgSO$_4$), filtered and concentrated under reduced pressure to give the crude product (70 mg). The crude product was purified by flash chromatography (silica gel, 20% EtOAc/hexane) to give 4-(4-chloro-2-methylphenyl)-2-phenylpyrimidine-5-carbaldehyde (63 mg, 75%) as a white solid.

$^1$H NMR (400 MHz, CDCl$_3$) 9.82 (s, 1H), 9.26 (s, 1H), 8.48 (dd, J=1.8, 8.4 Hz, 2H), 7.41-7.52 (m, 3H), 7.12-7.37 (m, 3H), 2.26 (s, 3H).

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=7.84 min, 90% homogeneity index.

LCMS: Anal. Calcd. for C$_{18}$H$_{13}$ClN$_2$O 308.07 found: 309.06 (M+H)$^+$.

Example 9

Step 4. 4-(4-Chloro-2-methylphenyl)-2-phenylpyrimidine-5-carbaldehyde oxime

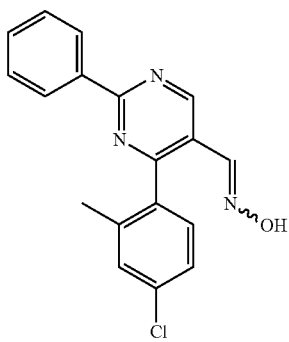

To a stirred solution of 4-(4-chloro-2-methylphenyl)-2-phenylpyrimidine-5-carbaldehyde (63 mg, 0.20 mmol) in EtOH (4 mL) was added NH$_2$OH.HCl (28.3 mg, 0.41 mmol) and pyridine (430 µL). The reaction was heated to 70° C. for 3 hrs and was concentrated under reduced pressure. The residue was dissolved in EtOAc (10 mL) and the organic layer was washed by saturated NH4Cl solution (10 mL) and brine, dried (MgSO$_4$), filtered and concentrated under reduced pressure to give the crude product as a light yellow foam (69 mg). The crude reaction product was moved onto next step without further purification.

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=8.26 min, 95% homogeneity index.

LCMS: Anal. Calcd. for C$_{18}$H$_{14}$ClN$_3$O 323.08 found: 324.06 (M+H)$^+$.

Example 9

Step 5. (4-(4-Chloro-2-methylphenyl)-2-phenylpyrimidin-5-yl)methanamine

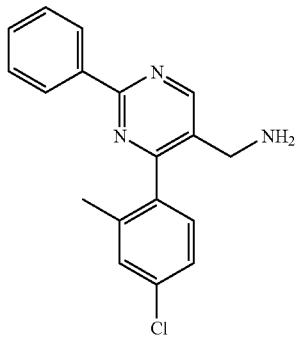

To a stirred solution (4-(4-chloro-2-methylphenyl)-2-phenylpyrimidin-5-yl)methanamine (69 mg, 0.21 mmol) in EtOH (5 mL) was added Zn (28 mg, 0.43 mmol), NH$_4$OAc (33 mg, 0.43 mmol) and NH$_4$OH (58 µL, 28% in H$_2$O, 0.43 mmol). The reaction was heated to 78° C. for 10 hrs. Additional 2 eqs of Zn, NH$_4$OAc, NH$_4$OH were added and after 3 hrs, the reaction was concentrated under reduced pressure and diluted with EtOAc (10 mL). The organic layer was washed by saturated NaHCO$_3$ solution solution (10 mL) and brine, dried (MgSO$_4$), filtered and concentrated under reduced pressure to give the crude product. The crude product was purified by reverse-phase preparative HPLC to provide (4-(4-chloro-2-methylphenyl)-2-phenylpyrimidin-5-yl)methanamine, TFA salt (27 mg, 40% for 2 steps) as a white solid.

$^1$H NMR (400 MHz, CD$_3$OD) 9.04 (s, 1H), 8.44 (dd, J=1.3, 8.3 Hz, 2H), 7.44-7.54 (m, 4H), 7.38 (dd, J=1.8, 6.2 Hz, 1H), 7.9 (d, J=7.9 Hz, 1H), 4.07 (s, 2H), 2.21 (s, 3H).

HPLC Phenomenex LUNA C-18 4.6×75 mm, 0 to 100% B over 8 minutes, 2 minutes hold time, A=90% water, 10% methanol, 0.2% phosphoric acid, B=10% water, 90% methanol, 0.2% phosphoric acid, RT=5.52 min, 99% homogeneity index.

LCMS: Anal. Calcd. for C$_{18}$H$_{16}$ClN$_3$ 309.10 found: 310.07 (M+H)$^+$.

HRMS: Anal. Calcd. for $C_{18}H_{17}ClN_3$ 310.1111 found: 310.1101 (M+H)⁺.

Example 10

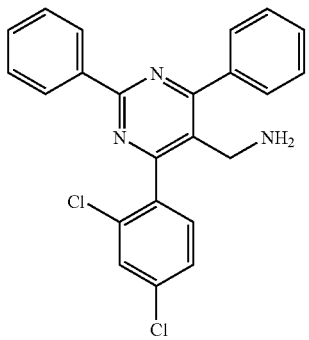

Example 10

Step 1. Diethyl 2-(2,4-dichlorobenzylidene)malonate

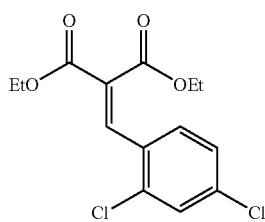

To a stirred solution of diethyl malonate (0.92 g, 5.71 mmol) in toluene (10 mL) was added 2,4-dichlorobenzaldehyde (1 g, 5.71 mmol), piperidine (23 μL, 0.23 mmol), acetic acid (13 μL, 0.23 mmol) and molecular sieves (3 Å). The reaction was heated to 70° C. for 2 days and was concentrated under reduced pressure. The residue was filtered through a pad of silica flushing with EtOAc/hexane (1:1) solution. The filtrate was concentrated to give diethyl 2-(2,4-dichlorobenzylidene)malonate (1.83 g, 97%) as a yellow oil.

¹H NMR (400 MHz, CDCl₃) 7.94 (s, 1H), 7.46 (d, J=2.2 Hz, 1H), 7.40 (d, J=7.0 Hz, 1H), 7.22 (dd, J=2.2, 7.0 Hz, 1H), 4.20-4.37 (m, 6H), 1.34 (t, J=J=7.0 Hz, 4.5 H), 1.24 (t, J=7.0 Hz, 4.5 H).

Example 10

Step 2. Ethyl 4-(2,4-dichlorophenyl)-6-oxo-2-phenyl-1,6-dihydropyrimidine-5-carboxylate

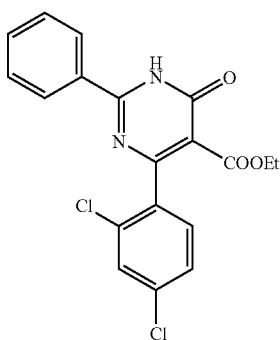

A solution of diethyl 2-(2,4-dichlorobenzylidene)malonate (300 mg, 0.91 mmol) and benzamidine (134 mg, 0.91 mmol) in EtOH (3 mL) was heated to 60° C. for 2 hrs. The reaction was concentrated under reduced pressure. The resulting residue was dissolved in CH₂Cl₂ (4 mL) and DDQ (238 mg, 1.05 mmol) was added. After 1 hr, The reaction was diluted with cyclohexane/EtOAc solution (4:1, 100 mL) and the organic layer was extracted with saturated NaHCO₃ solution (2×60 mL), brine (50 mL). The organic layer dried (MgSO₄), filtered and concentrated under reduced pressure to give ethyl 4-(2,4-dichlorophenyl)-6-oxo-2-phenyl-1,6-dihydropyrimidine-5-carboxylate (372 mg, 100%) as a yellow solid. This product was moved onto next step without further purification.

¹H NMR (400 MHz, CDCl₃) 8.32 (d, J=6.6 Hz, 2H), 7.32-7.63 (m, 6H), 4.16 (q, J=7.0Hz, 2H), 1.16 (t, J=7.0Hz, 3H).

Example 10

Step 3. Ethyl 4-chloro-6-(2,4-dichlorophenyl)-2-phenylpyrimidine-5-carboxylate

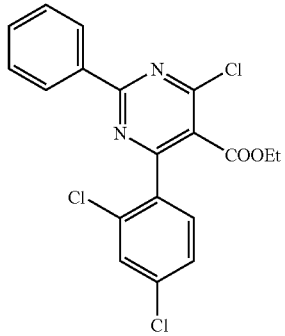

To a stirred solution of ethyl 4-(2,4-dichlorophenyl)-6-oxo-2-phenyl-1,6-dihydropyrimidine-5-carboxylate (372 mg, 0.91 mmol) in doixane (6 mL) was added POCl₃ (0.4 mL, 4.55 mmol) and N,N-dimethylaniline (11.5 μL, 0.09 mmol). After 4 hrs at 70° C., the reaction was concentrated under reduced pressure and diluted with EtOAc (100 mL). The organic layer was extracted with saturated NaHCO₃ solution (2×60 mL), brine (50 mL), dried (MgSO₄), filtered and concentrated under reduced pressure. The crude reaction product was purified by flash chromatography (silica gel, 30% EtOAc/hexane) to give ethyl 4-chloro-6-(2,4-dichlorophenyl)-2-phenylpyrimidine-5-carboxylate (360 mg, 97% for 3 steps) as a clear oil.

¹H NMR (400 MHz, CDCl₃) 8.48 (d, J=6.6 Hz, 2H), 7.47-7.58 (m, 6H), 4.21 (q, J=7.0 Hz, 2H), 1.12 (t, J=7.0 Hz, 3H).

Example 10

Step 4. Ethyl 4-(2,4-dichlorophenyl)-2,6-diphenylpyrimidine-5-carboxylate

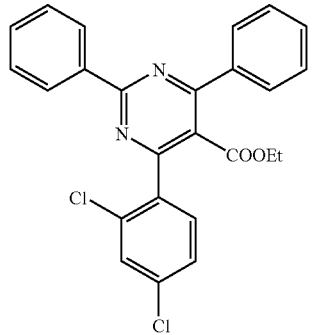

A solution of ethyl 4-chloro-6-(2,4-dichlorophenyl)-2-phenylpyrimidine-5-carboxylate (30 mg, 0.07 mmol) and phenyl boronic acid (14 mg, 0.11 mmol) in toluene (3 mL) was degassed with argon for 15 minutes. To this solution was added Pd(PPh$_3$)$_4$ (9 mg, 0.007 mmol), Na$_2$CO$_3$ (23 mg, 0.22 mmol) and the reaction was heated to reflux for 3 days. The reaction was diluted with EtOAc (20 mL) and extracted with saturated NH$_4$Cl solution (2×20 mL), brine (20 mL). The organic layer was dried (MgSO$_4$), filtered and concentrated under reduced pressure. The crude reaction product was purified by flash chromatography (silica gel, 20% EtOAc/hexane) to give ethyl 4-(2,4-dichlorophenyl)-2,6-diphenylpyrimidine-5-carboxylate (14 mg, 42%).

$^1$H NMR (400 MHz, CDCl$_3$) 8.58 (dd, J=1.3, 8.4 Hz, 2H), 7.80 (d, J=8.0 Hz, 2H), 7.46-7.57 (m, 7H), 7.36-7.43 (m, 2H), 4.00 (q, J=7.0 Hz, 2H), 0.91 (t, J=7.0 Hz, 3H).

Example 10

Steps 5-8. (4-(2,4-Dichlorophenyl)-2,6-diphenylpyrimidin-5-yl)methanamine

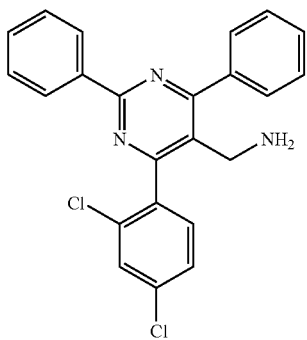

To a stirred solution of ethyl 4-(2,4-dichlorophenyl)-2,6-diphenylpyrimidine-5-carboxylate (14 mg, 0.03 mmol) in THF (2 mL) was added DIBAL-H (0.05 mL, 0.08 mmol). The reaction was kept at ambient temperature for 1 hr and then 50° C. for 1 hr and was quenched by sodium potassium tartrate solution (30%, 10 mL).). The reaction was diluted with EtOAc (15 mL) and the organic layer was washed with 1N NaOH (10 mL), saturated Na$_2$CO$_3$ solution (10 mL) and brine (10 mL), dried (MgSO$_4$), filtered and concentrated under reduced pressure. The crude reaction product was purified by flash chromatography (silica gel, 20% EtOAc/hexane) to give the alcohol (10 mg, 79%).

To a stirred solution of alcohol (10 mg, 0.025 mmol) in CH$_2$Cl$_2$ (2 mL) was added MsCl (4 μL, 0.049 mmol) and Et$_3$N (17 μL, 0.12 mmol). The reaction was kept at ambient temperature for 16 hrs and was quenched by addition of H$_2$O (5 mL). The organic layer was extracted with H$_2$O and brine, dried (MgSO$_4$), filtered and concentrated under reduced pressure to afford the desired mesylate. The crude reaction product was dissolve in DMF (2 mL) and NaN$_3$ (2.5 mg, 0.037 mmol) was added. The reaction was heated to 50° C. for 1 hr and was quenched by H$_2$O (5 mL). The aqueous layer was extracted with EtOAc (2×10 mL) and the combined organic layers were washed with brine, dried (MgSO$_4$), filtered and concentrated under reduced pressure to give the desired azide. The azide was dissolved in THF (1 mL) and H$_2$O (0.2 mL) and PPh$_3$ (polymer supported, 3 mmol/g, 16 mg, 0.049 mmol) was added. The reaction was heated to 50° C. for 1 hr and filtered to remove polymer support. The filtrated was concentrated under reduced pressure and purified by reverse-phase preparative HPLC to provide (4-(2,4-dichlorophenyl)-2,6-diphenylpyrimidin-5-yl)methanamine, TFA salt (5 mg, 50% for 3 steps) as a white solid.

$^1$H NMR (400 MHz, CD$_3$OD) 8.49 (dd, J=1.8, 8.4 Hz, 2H), 7.74-7.82 (m, 3H), 7.60-7.70 (m, 5H), 7.47-7.59 (m, 3H), 4.37 (d, J=14.5 Hz, 1H), 4.13 (d, J=14.5 Hz, 1H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.52 min, 99% homogeneity index.

LCMS: Anal. Calcd. for C$_{23}$H$_{17}$C$_{12}$N$_3$ 405.08 found: 406.19 (M+H)$^+$.

HRMS: Anal. Calcd. for C$_{23}$H$_{18}$C$_{12}$N$_3$ 406.0878 found: 406.0895 (M+H)$^+$.

Example 11

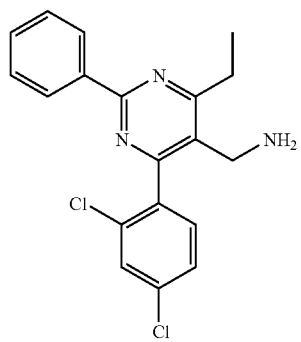

(4-(2,4-Dichlorophenyl)-6-ethyl-2-phenylpyrimidin-5-yl)methanamine, TFA salt was prepared by the methods described in Example 8, using methyl 3-oxopentanoate for Step 1.

$^1$H NMR (400 MHz, CD$_3$OD) 8.38 (dd, J=1.76, 6.16Hz, 1H), 7.64 (d, J=1.76 Hz, 1H), 7.37-7.53 (m, 6H), 4.17 (d, J=14.5 Hz, 1H), 3.89 (d, J=15.5 Hz, 1H), 2.99 (m, 2H), 1.43 (t, J=7.48 Hz, 3H).

HPLC Phenomenex LUNA C-18 4.6×50 mm, 0 to 100% B over 8 minutes, 2 minutes hold time, A=90% water, 10% methanol, 0.2% phosphoric acid, B=10% water, 90% methanol, 0.2% phosphoric acid, RT=5.84 min, 100% homogeneity index.

LCMS: Anal. Calcd. for C$_{19}$H$_{17}$C$_{12}$N$_3$ 357.08 found: 358.06 (M+H)$^+$.

LCMS: Anal. Calcd. for C$_{19}$H$_{18}$C$_{12}$N$_3$ 358.0878 found: 358.00884 (M+H)$^+$.

EXAMPLE 12

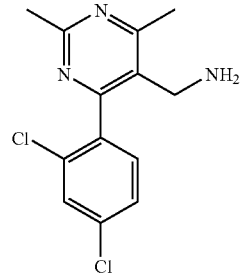

(4-(2,4-Dichlorophenyl)-2,6-dimethyl-pyrimidin-5-yl) methanamine, TFA salt was prepared by the methods described in Example 8, using acetamidine, hydrochloride for Step 2.

$^1$H NMR (400 MHz, CD$_3$OD) 7.60 (d, J=1.96 Hz, 1H), 7.45 (dd, J=1.96, 8.32 Hz, 1H), 7.36 (d, J=8.32 Hz, 1H), 4.11 (d, J=14.96 Hz, 1H), 3.83 (d, J=14.96 Hz, 1H), 2.61 (s, 3H), 2.60 (s, 3H).

HPLC Phenomenex LUNA C-18 4.6×50 mm, 0 to 100% B over 8 minutes, 2 minutes hold time, A=90% water, 10% methanol, 0.2% phosphoric acid, B=10% water, 90% methanol, 0.2% phosphoric acid, RT=3.10 min, 100% homogeneity index.

LCMS: Anal. Calcd. for C$_{13}$H$_{13}$C$_{12}$N$_3$ 281.05 found: 282.19 (M+H)$^+$.

HRMS: Anal. Calcd. for C$_{13}$H$_{14}$Cl$_2$N$_3$ 282.0565 found: 282.0569 (M+H)$^+$.

EXAMPLE 13

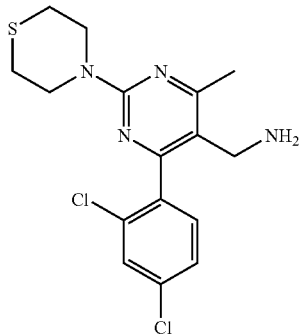

Example 13

Step 1. Methyl 2-(benzylthio)-4-(2,4-dichlorophenyl)-6-methyl-1,4-dihydropyrimidine-5-carboxylate

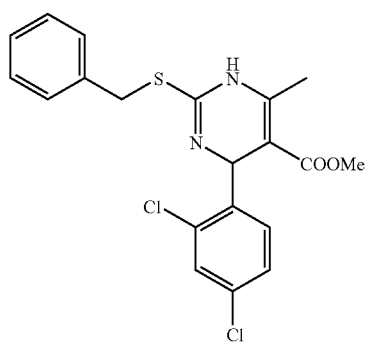

To a stirred solution of methyl 2-(2,4-dichlorobenzylidene)-3-oxobutanoate from Example 8, Step 1 (60 mg, 0.22 mmol) and benzylthiourea HCl salt (44 mg, 0.22 mmol) in DMF (2 mL) was added molecular sieves (3 Å). The reaction was heated to 90° C. for 16 hrs and was diluted with EtOAc (15 mL) and filtered to remove molecular sieves. The organic layer was extracted with H$_2$O (2×10 mL), brine, dried (MgSO$_4$), filtered and concentrated under reduced pressure to afford the desired methyl 2-(benzylthio)-4-(2,4-dichlorophenyl)-6-methyl-1,4-dihydropyrimidine-5-carboxylate. The crude reaction product (>95% purity) was moved onto next step without further purification.

Example 13

Step 2. Methyl 2-(benzylthio)-4-(2,4-dichlorophenyl)-6-methylpyrimidine-5-carboxylate

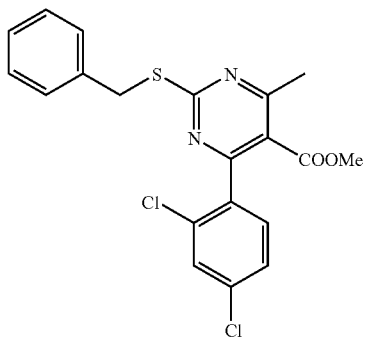

The crude methyl 2-(benzylthio)-4-(2,4-dichlorophenyl)-6-methyl-1,4-dihydropyrimidine-5-carboxylate (0.22 mmol) from Step 1 was dissolved in CH$_2$Cl$_2$ (2 mL) and DDQ (50 mg, 0.22 mmol) was added. After 1 hr, The reaction was diluted with cyclohexane/EtOAc solution (4:1, 10 mL) and the organic layer was extracted with saturated NaHCO$_3$ solution (2×6 mL), brine (5 mL). The organic layer dried (MgSO$_4$), filtered and concentrated under reduced pressure to give methyl 2-(benzylthio)-4-(2,4-dichlorophenyl)-6-methylpyrimidine-5-carboxylate. The crude reaction product (>95% purity) was moved onto next step without further purification.

$^1$H NMR (400 MHz, CDCl$_3$) 7.45 (d, J=1.3 Hz, 1H), 7.41 (d, J=6.2 Hz, 1H), 7.20-7.37 (m, 6H), 4.41 (s, 2H), 3.63 (s, 3H), 2.66 (s, 3H).

Example 13

Step 3. Methyl 2-(benzylsulfonyl)-4-(2,4-dichlorophenyl)-6-methylpyrimidine-5-carboxylate

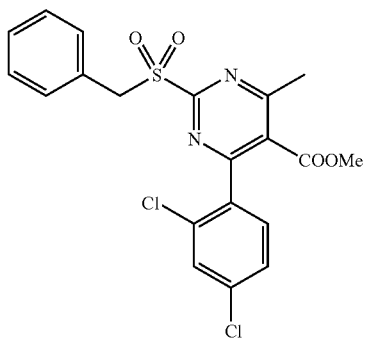

To crude methyl 2-(benzylthio)-4-(2,4-dichlorophenyl)-6-methylpyrimidine-5-carboxylate (0.22 mmol) from Step 2 in CH$_2$Cl$_2$ (3 mL) was added mCPBA (105 mg, 0.55 mmol). After 16 hrs, the reaction was concentrated under reduced pressure and diluted with EtOAc (10 mL). The organic layer was extracted with saturated NaHCO₃ solution (2×6 mL), brine (5 mL), dried (MgSO₄), filtered and concentrated under reduced pressure. The crude reaction product was purified by flash chromatography (silica gel, 20% EtOAc/hexane) to give methyl 2-(benzylsulfonyl)-4-(2,4-dichlorophenyl)-6-methylpyrimidine-5-carboxylate (80 mg, 80% for 3 steps) as a clear oil.

¹H NMR (400 MHz, CDCl₃) 7.51 (s, 1H), 7.26-7.42 (m, 7H), 4.80 (s, 2H), 3.72 (s, 3H), 2.79 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.48 min.

LCMS: Anal. Calcd. for $C_{20}H_{16}C_{12}N_2O_4S$ 450.02 found: 451.15 (M+H)⁺.

Example 13

Step 4. Methyl 4-(2,4-dichlorophenyl)-6-methyl-2-thiomorpholinopyrimidine-5-carboxylate

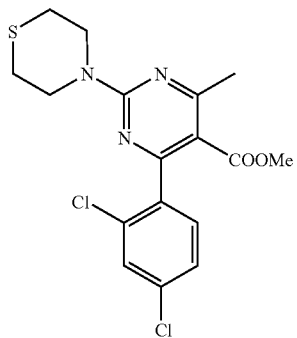

To a stirred solution of methyl 2-(benzylsulfonyl)-4-(2,4-dichlorophenyl)-6-methylpyrimidine-5-carboxylate (17 mg, 0.037 mmol) in dioxane (2 mL) was added thiomorpholine (4.5 mL, 0.045 mmol). After at 40° C. for 1 hr, the reaction was concentrated under reduced pressure and diluted with EtOAc (10 mL). The organic layer was extracted with saturated NaHCO₃ solution (2×6 mL), brine (5 mL), dried (MgSO₄), filtered and concentrated under reduced pressure to give methyl 4-(2,4-dichlorophenyl)-6-methyl-2-thiomorpholinopyrimidine-5-carboxylate (15 mg, 100%). The crude reaction product (>98% purity) was moved onto next step without further purification.

¹H NMR (400 MHz, CDCl₃) 7.43 (d, J=1.8 hz, 1H), 7.31 (dd, J=1.8, 8.4 Hz, 1H), 7.22 (d, J=8.4 Hz, 1H), 4.21 (m, 4H), 3.55 (s, 3H), 2.66 (m, 4H), 2.58 (s, 3H).

Example 13

Step 5-8. (4-(2,4-Dichlorophenyl)-6-methyl-2-thiomorpholinopyrimidin-5-yl)methanamine, TFA Salt

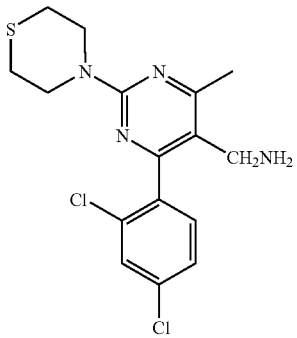

(4-(2,4-Dichlorophenyl)-6-methyl-2-thiomorpholinopyrimidin-5-yl)methanamine, TFA salt was prepared by the methods described in Example 10, Step 5-8.

¹H NMR (400 MHz, CD₃OD) 7.67 (d, J=1.2 Hz, 1H), 7.52 (dd, J=1.2, 7.6 Hz, 1H), 7.40 (d, J=7.6 Hz, 1H), 4.17 (m, 4H), 4.06 (d, J=15.2 Hz, 1H), 3.78 (d, J=15.2 Hz, 1H), 2.63 (m, 4H), 2.53 (s, 3H).

HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=3.37 min, 95% homogeneity index.

LCMS: Anal. Calcd. for $C_{16}H_{18}C_{12}N_4S$ 368.06 found: 369.18 (M+H)⁺.

We claim:

1. A compound of formula (I)

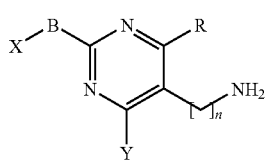

(I)

wherein:

n = 1;

R is a substituent selected from the group consisting of hydrogen (H), halogen, cyano (CN), $CF_3$, alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl and cycloheteroalkylalkyl, wherein any such substituent may optionally be substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

B is a bond;

X is a substituent selected from the group consisting of hydrogen (H), alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroarylalkyl, saturated cycloheteroalkyl and cycloheteroalkylalkyl, wherein any such substituent may optionally be substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; or B—X taken together can be a halogen; and Y is aryl, optionally substituted with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

including pharmaceutically acceptable salts thereof, and all stereoisomers thereof.

2. The compound as defined in claim 1 selected from

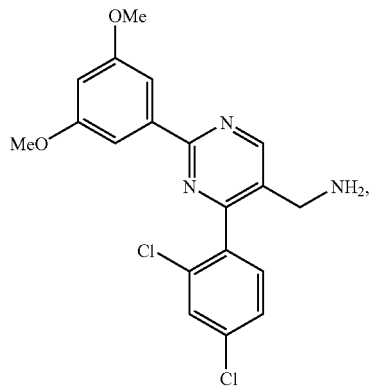

-continued

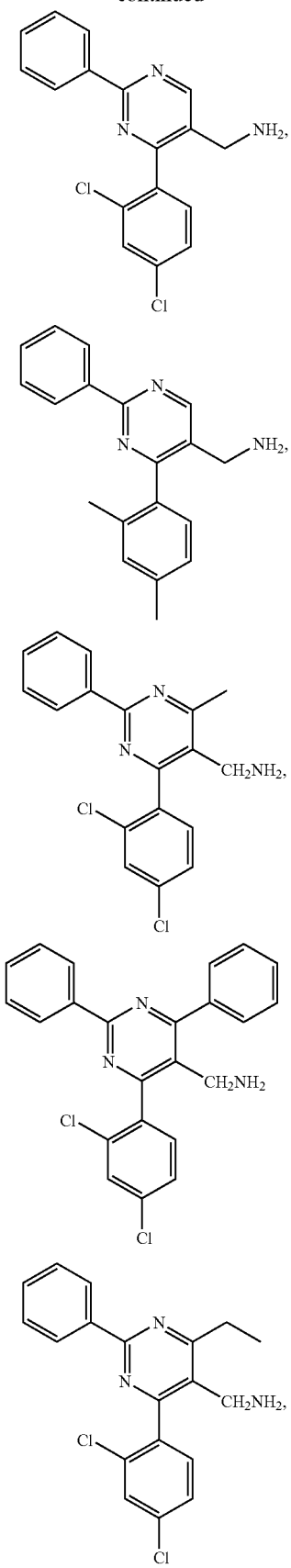

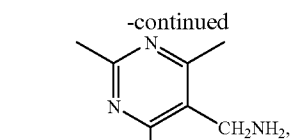

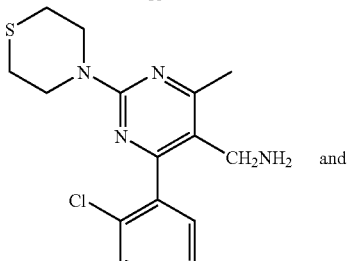

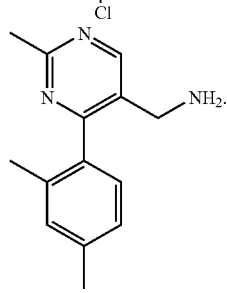

3. A pharmaceutical composition comprising a compound as defined in claim 1 and a pharmaceutically acceptable eater therefor.

4. A pharmaceutical combination comprising a compound of formula I as defined in claim 1 and at least one therapeutic agent selected from the group consisting of an antidiabetic agent, an anti-obesity agent, a anti-hypertensive agent, an anti-atherosclerotic agent and a lipid-lowering agent.

5. The pharmaceutical combination as defined in claim 4 wherein the therapeutic agent is an antidiabetic agent.

6. The combination as defined in claim 5 wherein the antidiabetic agent is at least one agent selected from the group consisting of a biguanide, a sulfonyl urea, a glucosidase inhibitor, a PPAR gamma agonist, a PPAR alpha/gamma dual agonist, an aP2 inhibitor, a SGLT2 inhibitor, an insulin sensitizer, a glucagon-like peptide-1 (GLP-1), insulin and a meglitinide.

7. The combination as defined in claim 6 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, isaglitazone, repaglinide and nateglinide.

8. The combination as defined in claim 5 wherein the compound of formula I is present in a weight ratio to the antidiabetic agent in the range of about 0.01 to about 300:1.

9. The combination as defined in claim 4 wherein the anti-obesity agent is at least one agent selected from the group consisting of a beta 3 adrenergic agonist, a lipase inhibitor, a serotonin (and dopamine) reuptake inhibitor, a thyroid receptor beta compound and an anorectic agent.

10. The combination as defined in claim 9 wherein the anti-obesity agent is at least one agent selected from the group consisting of orlistat, sibutramine, topiramate, axokine, dexamphetamine, phentermine, phenylpropanolamine and mazindol.

11. The combination as defined in claim 4 wherein the lipid lowering agent is at least one agent selected from the group consisting of an MTP inhibitor, cholesterol ester transfer protein, an HMG CoA reductase inhibitor, a squalene synthetase inhibitor, a fibric acid derivative, an upregulator of LDL receptor activity, a lipoxygenase inhibitor, or an ACAT inhibitor.

12. The combination as defined in claim 11 wherein the lipid lowering agent is at least one agent selected from the group consisting of pravastatin, lovastatin, simyastatin, atorvastatin, cerivastatin, fluvastatin, nisvastatin, visastatin, fenofibrate, gemfibrozil, clofibrate and avasimibe.

13. The combination as defined in claim 4 wherein the compound of formula I is present in a weight ratio to the lipid-lowering agent in the range of about 0.01 to about 100:1.

14. A method for treating Type II diabetes or hyperglycemia, which comprises administering to a mammalian species in need of treatment a therapeutically effective amount of a compound as defined in claim 1.

15. A method according to claim 14 further comprising administering, concurrently or sequentially, a therapeutically effective amount of at least one additional therapeutic agent selected from the group consisting of an antidiabetic agent, an anti-obesity agent, a anti-hypertensive agent, an anti-atherosclerotic agent, an agent for inhibiting allograft rejection in transplantation and a lipid-lowering agent.

* * * * *

UNITED STATES PATENT AND TRADEMARK OFFICE
CERTIFICATE OF CORRECTION

| | | |
|---|---|---|
| PATENT NO. | : 7,589,088 B2 | Page 1 of 1 |
| APPLICATION NO. | : 11/314795 | |
| DATED | : September 15, 2009 | |
| INVENTOR(S) | : Meng et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C 154(b) by 857 days.

Signed and Sealed this
Eighteenth Day of January, 2011

David J. Kappos
*Director of the United States Patent and Trademark Office*

UNITED STATES PATENT AND TRADEMARK OFFICE
CERTIFICATE OF CORRECTION

PATENT NO. : 7,589,088 B2
APPLICATION NO. : 11/314795
DATED : September 15, 2009
INVENTOR(S) : Wei Meng et al.

It is certified that error appears in the above-identified patent and that said Letters Patent is hereby corrected as shown below:

In the Claims:

Claim 3:

Column 54, line 39, change "eater" to -- carrier --.

Claim 6:

Column 54, line 53, change "(GLP-l)" to -- (GLP-1) --.

Claim 7:

Column 54, line 59, change "chiorpropamide" to -- chlorpropamide --.

Claim 12:

Column 55, line 18, change "simyastatin" to -- simvastatin --.

Signed and Sealed this
First Day of November, 2011

David J. Kappos
*Director of the United States Patent and Trademark Office*